US009663560B2

(12) United States Patent
Abdurakhmonov et al.

(10) Patent No.: US 9,663,560 B2
(45) Date of Patent: May 30, 2017

(54) **COTTON *PHYA1 RNAI* IMPROVES FIBER QUALITY, ROOT ELONGATION, FLOWERING, MATURITY AND YIELD POTENTIAL IN *GOSSYPIUM HIRSUTUM* L**

(75) Inventors: Ibrokhim Y. Abdurakhmonov, Tashkent (UZ); Zabardast T. Buriev, Tashkent (UZ); Abdusattor Abdukarimov, Tashkent (UZ); Sukumar Saha, Starkville, MS (US); Johnie N. Jenkins, Starkville, MS (US); Alan E. Pepper, College Station, TX (US)

(73) Assignees: The United States of America, as represented by the Secretary of Agriculture, Washington, DC (US); Agriculture Center of Genomics and Bioinformatics, Academy of Sciences Of Uzbekistan, Tashkent (UZ); The Texas A & M University System, College Station, TX (US)

( * ) Notice: Subject to any disclaimer, the term of this patent is extended or adjusted under 35 U.S.C. 154(b) by 359 days.

(21) Appl. No.: 13/445,696

(22) Filed: Apr. 12, 2012

(65) Prior Publication Data

US 2013/0227723 A1    Aug. 29, 2013

(30) Foreign Application Priority Data

Feb. 28, 2012 (UZ) .................................. 20120069

(51) Int. Cl.
| | | |
|---|---|---|
| *C12N 15/82* | (2006.01) | |
| *A01H 5/00* | (2006.01) | |
| *A01H 5/10* | (2006.01) | |
| *C07K 14/415* | (2006.01) | |

(52) U.S. Cl.
CPC ........ *C07K 14/415* (2013.01); *C12N 15/8218* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 6,506,559 B1 * | 1/2003 | Driver ................ | A61K 31/7105 435/325 |
| 2009/0285784 A1 * | 11/2009 | Raemaekers .......... | A01N 57/16 424/93.2 |

OTHER PUBLICATIONS

Abdurakhmonov et al, 2010, BMC Plant Bio, 10:1-18.*
Ibarra et al, 2013, Mol. Plant, Transcriptional Programs Related to Photochrome A Function in Arabidopsis Seed Germination: 1-14.*
Kay et al, 1987, Science, 236:1299-1302.*
Helliwell et al, 2002, Funct. Plant BIol., 29: 1217-1225.*
Sunilkumar et al, 2001, Mol. Breeding, 8:37-52.*
Abdurakhmonov et al, 2007, J. of Heredity, 98:258-266.*

* cited by examiner

*Primary Examiner* — Jason Deveau Rosen
(74) *Attorney, Agent, or Firm* — John D. Fado; Gail Poulos

(57) ABSTRACT

Improvement of fiber quality of Upland cultivars (*Gossypium hirsutum*), while maintaining early maturity and productivity, is a fundamental problem in conventional cotton breeding. Phytochromes play a fundamental role in plant development, flowering and cotton fiber length. Targeted RNAi of PHYA1 genes in cotton suppressed expression of PHYA1 and/or PHYB, resulting in over-expression of the remaining PHYA2/B/C/E genes. This altered expression induced a number of phytochrome-associated phenotypes, including increased root length and mass, increased anthocyanin-pigment, vigorous shoot development and vegetative growth, early flowering, early boll maturity, increased fiber length and increased seed cotton yield compared to control plants. These RNAi phenotypes were stably inherited and expressed through four generations ($T_{0-3}$) and were transferable from RNAi Coker-312 plants to Upland cultivars via conventional hybridization.

19 Claims, 9 Drawing Sheets
(7 of 9 Drawing Sheet(s) Filed in Color)

COTTON *PHYA1 RNAI* IMPROVES FIBER QUALITY, ROOT ELONGATION, FLOWERING, MATURITY AND YIELD POTENTIAL IN *GOSSYPIUM HIRSUTUM* L

BACKGROUND OF THE INVENTION

Field of the Invention

This invention relates to the role of phytochrome genes in the regulation of flowering, fiber initiation and elongation, and other characteristics affected by altered photomorphogenesis in *Gossypium* plants; PHYA1 gene silencing constructs comprising polynucleotides encoding phytochrome A1 proteins, transgenic cotton plants comprising the PHYA1 RNAi polynucleotides, and a method of using RNA interference of the phytochrome PHYA1 gene to generate novel transgenic plants exhibiting improved cotton fiber quality, early-flowering and early boll maturity, enhanced root elongation, and increased seed cotton production due to both the suppression of PHYA1 and the several fold increases in the expression of other phytochrome genes.

Description of the Relevant Art

Light is one of the most important environmental factors controlling plant development and physiology. It affects virtually all aspects of plant growth, from seed germination to vegetative morphology, floral initiation, control of circadian rhythms, gene regulation and expression, gravitropism and phototropism (Fankhauser and Chory. 1997. *Ann. Rev. Cell Dev. Biol.* 13:203-229; Furuya and Kim. 2000. *Trends in Plant Sci.* 3:87-88; Tepperman et al. 2001. *Proc. Natl. Acad. Sci. USA* 98(16):9437-9442). Plants respond to light through several photoreceptor systems. The phytochrome photoreceptor gene family is best characterized in the model plant *Arabidopsis*, which has five phytochrome genes PHYA, PHYB, PHYC, PHYD, and PHYE (Sharrock and Quail. 1989. *Genes and Dev.* 3:1745-1757; Clack et al. 1994. *Plant Mol. Biol.* 25:413-427; Cowl et al. 1994. *Plant Physiol.* 106:813-814). The phytochromes interact with cryptochromes, the circadian clock, phytohormones, and other signals to regulate floral initiation (Devlin et al. 1998. *Plant Cell* 10:1479-1487; Devlin et al. 1999. *Plant Physiol.* 119:909-915; Koornneef et al. 1997. *Plant Cell & Environ.* 20:779-784; Koornneef et al. 1998. *Ann. Rev. Plant Physiol. Plant Mol. Biol.* 49:345-370). In *Arabidopsis*, PHYA promotes plant flowering. A mutation in this gene causes a late flowering phenotype in *Arabidopsis* (Neff and Chory. 1998. *Plant Physiol.* 118:27-35). In contrast, PHYB is an inhibitor of flowering induction (Koornneef et al. 1998, supra; Reed et al. 2000. *Plant Physiol.* 122:1149-1160). Mutations in PHYB cause early flowering in both short (SD) and long (LD) day conditions in *Arabidopsis* (Bagnall et al. 1995. *Plant Physiol.* 108: 1495-1503), pea (Mockler et al. 1999. *Dev.* 106:2073-2082) and sorghum (Childs et al. 1997. *Plant Physiol.* 97:714-719). Plants overexpressing PHYA, being hyposensitive to photoperiod, exhibit light-dependent dwarfism, darker green leaves, reduced apical dominance and an early flowering phenotype in both SD and LD conditions (Bagnall et al., supra). PHYB/D/E overexpression correlates with shortening of hypocotyl length (Clough et al. 1995. *Plant Physiol.* 109:1039-1045; Devlin et al. 1999, supra; Devlin et al. 1998, supra; Lin, C. 2000. *Plant Physiol.* 1239:39-50) and an early flowering phenotype, as is observed, for example, in phyb mutants, suggesting more complex action mechanisms for PHYB (Bagnall et al., supra; Lin, supra). PHYC also contributes to photoperiodic flowering and natural phenotypic variation in flowering time in *Arabidopsis* (Franklin et al. 2003. *Plant Cell* 15:1981-1989; Monte et al. 2003. *Plant Cell* 15:1962-1980; Balasubramanian et al. 2006. *Nat. Genet.* 38:711-715). Additionally, phytochrome genes regulate vegetative plant growth parameters such as height, leaf and rosette production (Bagnall et al., supra).

In cultivated cottons, the phytochrome gene family has additional importance because there is evidence that the far red/red (FR/R) photon ratio influences length and diameter of developing fiber. For example, cotton fibers that were exposed to a high far red/red photon ratio were longer than those exposed to elevated photosynthetic light (Kasperbauer, M. J. 1994. *Physiol. Plantarum* 91:317-321; Kasperbauer, M. J. 2000. *Crop Sci.* 40:1673-1678). Genetic improvement of fiber yield and fiber quality, i.e., fiber length and fiber strength, is the primary objective of cotton breeding programs worldwide (Perkins et al. 1984. *In: Cotton Agron. Monogr.* Kohel and Lewis, Eds., ASA, CSSA, and SSSA, Madison, Wis., pp. 437-509). Fiber quality has become a major issue in recent years because of the technological changes in the textile industry (Perkins et al., supra; El-Mogahzy and Chewning. 2001. In: *Cotton Fiber to Yarn Manufacturing Technology*. Cotton Incorporated, Cary, N.C.). Pima (*Gossypium barbadense*) cotton fibers are fine, genetically stronger, and more uniform than the widely grown, early maturing and high yielding Upland (*Gossypium hirsutum*) cottons (El-Mogahzy and Chewning, supra). Finding an easy way to improve fiber properties of Upland cultivars, while maintaining yield and early maturity, is a fundamental problem to be solved in conventional cotton breeding worldwide.

Thus, there is a need for the development of improved cultivated cotton plants which produce high yields of quality cotton fibers which exhibit improved fiber length and fiber strength.

SUMMARY OF THE INVENTION

We have discovered that RNA interference of the cotton PHYA1 gene results in both the suppression of the targeted PHYA1 gene and also a several-fold increase in the expression of other phytochrome genes; that this alteration in the cotton phytochrome gene family expression profile results in a changed plant architecture with elongated leaf petioles, fruit branches, boll peduncles and root system, vigorous vegetative growth, early flowering and early boll maturity, senescence-enhanced anthocyanin pigmentation in stems and leaves, increased fiber quality (length, strength, micronaire, etc.) and fiber yield phenotypes; and that the changes are stably expressed in subsequent generations and transferable from the transformed Coker 312 genotype to Upland cultivar through genetic hybridization and selection.

In accordance with this discovery, it is an object of the invention to provide a strategy for effective endogenous gene silencing of the PHYA1 gene in cotton in order to alter photomorphogenesis in *Gossypium* plants.

It is a further object of the invention to provide a novel isolated or recombinant polynucleotide molecule comprising a DNA sequence encoding a portion of the hinge region of the PHYA1 polypeptide of *Gossypium hirsutum*.

It is another object of the invention to provide an isolated or recombinant polynucleotide molecule comprising a DNA sequence comprising a 213 base pair consecutive nucleotide molecule encoding a portion of the hinge region of the PHYA1 polypeptide.

It is an additional object of the invention to provide a hairpin nucleic acid construct encoding a PHYA1 polynucleotide gene sequence comprising a 213 consecutive sense nucleotide portion (SEQ ID NO:1) of the hinge region of the PHYA1 gene of Gossypium and the antisense-complement thereof, such that the first and the second polynucleotide sequences hybridize when transcribed into a ribonucleic acid to form the hairpin-like double stranded ribonucleotide molecule.

It is an additional object of the invention to provide a method for reducing the level of phytochrome A1 in a cotton plant, the method comprising expressing in the plant a heterologous nucleic acid construct encoding a PHYA1 gene sequence comprising a 213 bp consecutive sense nucleotide portion of the PHYA1 gene of Gossypium and the antisense-complement thereof, wherein the expressing induces RNA interference (RNAi) in the plant resulting in plants which produce elongated leaf petioles, fruit branches, boll peduncles and root system, vigorous vegetative growth, early flowering and early boll maturity, senescence-enhanced anthocyanin pigmentation in stems and leaves, increased fiber quality (length, strength, micronaire, uniformity, etc.) and fiber yield phenotypes relative to the wild-type cotton plant in the normal solar light.

It is a further object of the invention to provide a method for modifying or suppressing the expression of the PHYA1 gene in Gossypium sp. cells, the method comprising: transforming a plant with a vector comprising a nucleic acid sequence encoding a dsRNA and operatively linked to a promoter and a transcription termination sequence, selecting for transformed plants that have integrated the nucleic acid sequence into their genomes, screening the transformed plants for expression of the dsRNA encoded by the nucleic acid sequence, and selecting plants that express the dsRNA and/or siRNA.

It is another object of the invention to provide recombinant nucleotide sequences comprising a binary vector, the PHYA1 RNAi construct wherein the PHYA1 RNAi construct comprises a 213 bp nucleotide sequence from the hinge region of PHYA1 gene, wherein 35S promoter of Cauliflower mosaic virus (CaMV) is present in the nucleotide sequence immediately upstream of PHYA1 hairpin, each construct delivered by Agrobacterium-mediated inoculation, resulting in recombination in vitro, and the suppression of PHYA1 genes and altered expression levels of other phytochromes.

It is another object of the invention to provide a host cell comprising the PHYA1 RNAi binary vector construct.

It is an additional object of the invention to provide a method for producing a transgenic cotton plant wherein the cotton PHYA1 gene is suppressed, the method comprising: (a) stably transforming a host cotton plant cell with the PHYA1 RNAi construct of the invention, (b) somatically regenerating a transgenic plant from the stably transformed host cotton plant cell; and (c) growing the transgenic plant under conditions whereby said plants exhibit altered photomorphogenic characteristics including changed plant architecture with longer leaf petioles, fruit branches and boll peduncles, enhanced elongation of root system, vigorous vegetative growth, early flowering and early boll maturity, senescence-enhanced anthocyanin pigmentation in stems and leaves compared to wild-type non-transformed cotton plant.

It is an additional object of the invention to provide a transgenic cotton plant, produced by the methods of the invention, or the progeny thereof, comprising: the PHYA1 RNAi construct of the invention, said plants exhibiting altered expression of photomorphogenic characteristics including changed plant architecture with longer leaf petioles and fruit branches, enhanced elongation of root system, vigorous vegetative growth, early flowering and early boll maturity, senescence-enhanced anthocyanin pigmentation in stems and leafs compared to wild-type non-transformed cotton plant.

It is an additional object of the invention to provide a transgenic cotton cell comprising the PHYA1 RNAi construct of the invention.

It is an additional object of the invention to provide a transgenic cotton plant comprising the PHYA1 RNAi construct of the invention, wherein the transgenic plant exhibits cotton fibers of increased length and strength as well as improved micronaire, elongation and fiber uniformity relative to the wild-type cotton plant.

It is an additional object of the invention to provide a transgenic seed of the transgenic plant above, comprising the PHYA1 RNAi construct of the invention.

It is yet another object of the invention to provide plants, plant cells, and plant parts, and plant seeds which have been transformed by the PHYA1 RNAi construct of the invention.

It is another object of the invention to provide a method of inducing the superior fiber quality with increased length and strength and improved micronaire, elongation and fiber uniformity, increased seed cotton yield in a cotton plant, relative to the wild-type cotton plant, comprising suppression of the PHYA1 gene.

It is another object of the invention to provide a method of initiating early flowering and early boll maturation in a cotton plant, relative to the wild-type cotton plant, comprising suppression of the PHYA1 gene.

It is an additional object of the invention to provide a method of enhancing the root development of the cotton plant, relative to the wild-type cotton plant, comprising suppression of the PHYA1 gene.

It is an additional object of the invention to provide a method of enhancing vigorous vegetative growth, senescence-enhanced anthocyanin pigmentation in stems and leaves, and elongating leaf petioles, fruit branches and the peduncle of bolls of the cotton plant, relative to the wild-type cotton plant, comprising suppression of the PHYA1 gene.

It is an additional object of the invention to provide a method of altering plant characteristics by altering the number of copies of PHYA1 RNAi constructs of the invention in order to enhance suppression.

It is an additional object of the invention to provide a method of altering plant characteristics by altering the number of copies of PHYA1 RNAi constructs of the invention in order to enhance expression of the PHYB/C/E gene.

It is an additional object of the invention to provide a transgenic cotton cell comprising the PHYA1 RNAi construct of the invention, wherein the transgenic plant regenerated from said cell exhibits suppression of the PHYA1 gene and overexpression of the PHYB/C/E genes resulting in a plant demonstrating changed plant architecture with longer leaf petioles and fruit branches, an enhanced elongation of root system, vigorous vegetative growth, early flowering and early boll maturity, senescence-enhanced anthocyanin pigmentation in stems and leaf plates, superior fiber quality with increased length and strength and improved micronaire, elongation and fiber uniformity, and increased seed cotton yield, relative to the wild-type cotton plant.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1A is a schematic representation of PHYA gene, RNAi fragment position, and pHellsgate-8::PHYA1 RNAi plasmid; FIG. 1B depicts shoot and root development; and FIG. 1C depicts fiber length characteristics of $T_0$-generation PHYA1 RNAi and control cotton plants, somatically regenerated in tissue culture.

FIGS. 2A-2D show phytochrome-associated developmental changes in PHYA1 RNAi plants compared to controls: FIG. 2A shows the enhanced vegetative growth and early flowering in the $T_0$ RNAi plant compared to the same-day planted control plant, regenerated via somatic embryogenesis. FIG. 2C shows early flowering in the $T_1$ generation RNAi plant compared to the control plant (FIG. 2B) planted the same day in the same environment. FIG. 2D shows the difference in petiole length ($T_0$) and FIG. 2E shows the difference in root development ($T_3$) compared to the Coker-312 control.

FIG. 4A shows senescence-associated anthocyanin pigmentation in the field grown plants; FIGS. 4B and 4D show anthocyanin accumulation in leaf plates and cotton bolls and the elongation of leaf petioles and the peduncle of bolls; and FIG. 4C demonstrates the bush type and productivity of the RNAi line developed using this invention.

FIG. 6A depicts the upper half mean (UHM); FIG. 6B, the micronaire (MIC); FIG. 6C, fiber strength (STR); FIG. 6D, fiber uniformity; FIG. 6E, fiber elongation (ELO); FIG. 6F, average hypocotyl length; FIG. 6G, average number of flowers by Jul. 15, 2009; and FIG. 6H, average number of opened bolls by Sep. 15, 2009. Statistical significance of measured traits between RNAi genotypes and control in Wilcoxon matched-pairs signed-rank test at p≤0.05 was defined with "a", "b", and "c" letters.

DETAILED DESCRIPTION OF THE INVENTION

Figure 1:
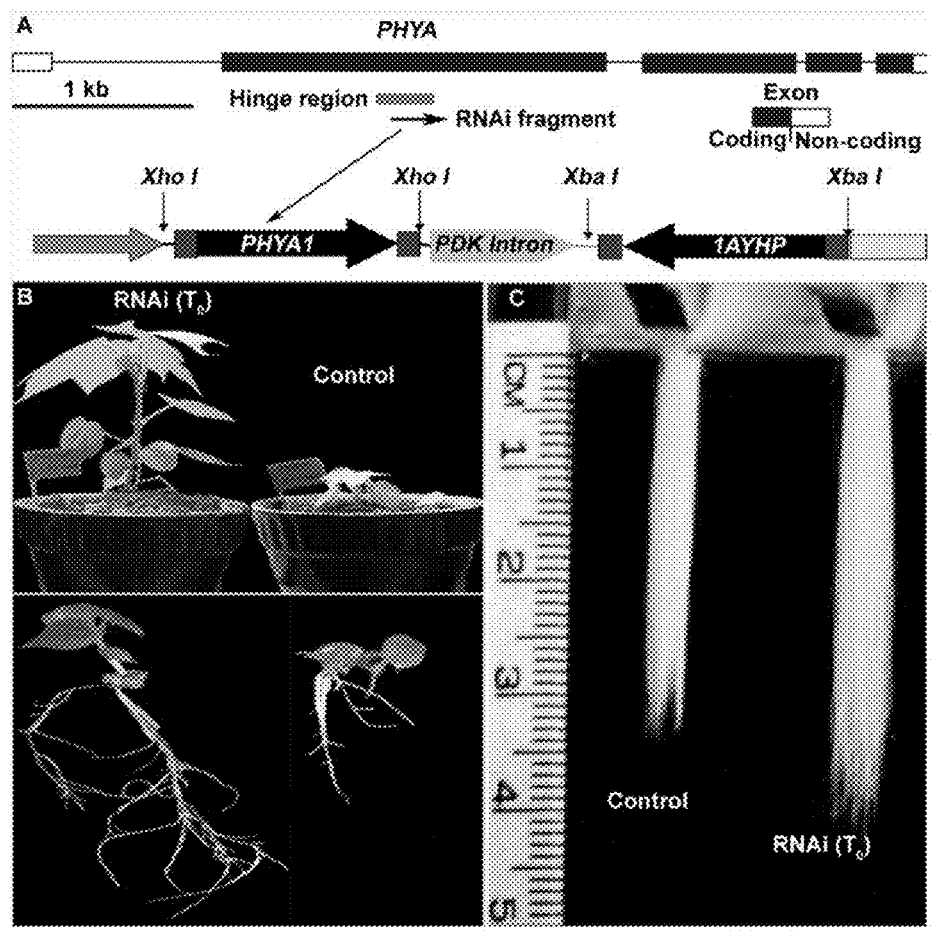
FIGS. 1A-1C depict the effects of PHYA1 RNAi in cotton.

This invention concerns the role of phytochrome genes in the regulation of particular phenotypic traits in cotton. We had hypothesized a role for phytochrome genes in the regulation of cotton fiber elongation (Abdurakhmonov, I. Y. 2001. Thesis. Texas A&M University, USA) based on the findings that our initial efforts on mapping phytochromes genes in a fiber length segregating bi-parental population suggested a significant association of PHYA1 gene polymorphisms with the fiber length Quantitative Trait Locus (QTL) (Abdurakhmonov 2001, supra). Using conserved sequences of a hinge region of phytochrome genes in angiosperms, in particular, phylogenetically closely related eudicot plants (belonging to asterids and rosids) such as *Arabidopsis*, tomato, potato, citrus, radish, carrot and other vegetable, fruit, oil, and fodder crops, we succeeded to clone and sequence cotton orthologs of the plant phytochrome gene family (Abdurakhmonov 2001, supra; Abdurakhmonov 2010, supra). We have recently reported on our studies of the molecular-evolutionary characterization of the phytochrome gene family in cotton (Abdurakhmonov et al. 2010. *BMC Plant Biol.* 10:119). Others have shown that RNA-induced gene silencing technology is a successful tool for investigating gene function in several organisms including plants (Waterhouse and Helliwell. 2003. *Nature Reviews Genetics* 4:29-38; Wesley at al. 2001. *The Plant Journal* 27:581-590; Helliwell et al. 2002. *Funct. Plant Biol.* 29:1217-1225).

We have investigated the effects of gene-silencing via RNA interference of phytochrome genes in cotton plants. In particular, we have investigated the effect of RNAi on the generation of longer cotton fiber and on improvements in other important fiber quality traits, in light of previously studied genetic correlations among fiber traits. Change in phytochrome gene expression affects timing of flowering. The effects of RNA interference of phytochrome genes on root and shoot development were also evaluated because previous studies had suggested the involvement of plant phytochrome genes in regulation of nitrate reductase (Jonassen et al. 2008. *Planta* 227(3):559-564; Lillo, C. 2008. *Biochem J.* 415(1):11-19) and salt tolerance homolog 2 and homolog 3 (Datta et al. 2007. *Plant Cell* 19(10):3242-3255; Datta et al. 2008. *Plant Cell* 20(9):2324-2338). In addition, there have been several reports on involvement of phytochromes and its signal transduction factors in cold/freezing and drought tolerance in *Arabidopsis* (Kim et al. 2002. *Plant J.* 29(6):693-704; Franklin and Whitelam. 2007. *Nat. Genet.* 39(11)1410-1413; Beck et al. 2007. *J. Biosci.* 32(3): 501-510).

We had previously characterized all cotton phytochromes and studied their molecular evolution in the cotton genome (Abdurakhmonov 2001, supra; Abdurakhmonov et al. 2010, supra). Two paralogous PHYA1 and PHYA2 genes were identified in diploid cottons resulting from a Malvaceae-specific gene duplication approximately 14 million years ago (MYA), before the divergence of the A and D genome ancestors. A single gene copy of PHYB, PHYC and PHYE was detected in diploid cottons. The cottons with allotetraploid genomes (AD) have largely retained the complete gene complements, with at least four PHYA genes and two genes encoding PHYB, PHYC and PHYE. The PHYD gene was not found in any cotton genomes examined (Abdurakhmonov et al. 2010, supra).

Here, we report our results from our studies on the biological role of phytochrome genes via RNA interference (RNAi) using the fiber quality QTL-associated PHYA1 gene sequence. We provide here the first molecular evidence on the importance of photomorphogenesis-related factors in the complex cotton fiber development process and the usefulness of phytochrome-specific RNAi in improving important agronomic traits of cotton. Further, we show that these effects can be transferred through sexual crosses to Upland cultivars.

In this work, we were able to induce phytochrome-associated RNAi phenotypes of cotton that generated several improved complex agronomic traits which are recognized to be important for cotton breeding but which had been challenging to accomplish through conventional breeding. Characterization of a hinge region of cotton phytochrome A, B, C and E (Abdurakhmonov 2001, supra; Abdurakhmonov et al. 2010, supra) and the significant association of PHYA1 genes with fiber quality prompted us to choose and use a PHYA1-specific sequence for developing the RNAi construct. The chosen 213 bp long PHYA1 fragment shared 87% nucleotide similarity with cotton PHYA2 genes, 75% nucleotide similarity with *Arabidopsis* PHYA, 59% nucleotide similarity with cotton PHYB genes, 53% nucleotide similarity with cotton PHYE genes and ~50% nucleotide similarity with cotton PHYC genes. Effective gene silencing requires typically 80-100% nucleotide identity to induce strong and specific RNAi (Holzberg et al. 2002. *Plant J.* 30:315-327); therefore, our RNAi construct was designed to preferentially target PHYA genes of cotton.

Our results on cotton transformation revealed interesting phytochrome-associated phenotypes in early embryonic plantlets. For example, we observed vigorous shoot and lateral root development as well as an early flowering phenotype. Such a vigorous lateral root development was observed with mutations in the HY5 gene in *Arabidopsis*; HY5 is a positive regulator of photomorphogenesis (Oyama et al. 1997. *Genes Dev.* 11:2983-2995). Given that cotton fibers develop from seed epidermis and thus anatomically resemble epidermal root tips, the observation of the root elongation process in $T_0$ PHYA1 RNAi plants is important for evaluating the presence of longer fibers in the same plants. Indeed, our results demonstrated a significant but variable improvement in fiber length as well as other fiber quality characteristics in different RNAi cotton families, which were stably expressed in subsequent $T_1$, $T_2$ and $T_3$ generation plants, grown under experimentally controlled field conditions under normal solar light. Our results agree with earlier observations on the effect of increased far red/red light ratios in fiber length and diameter (Kasperbauer 2000, supra) and our preliminary results on the association of PHYA1 with fiber length QTL in cotton (Abdurakhmonov 2001, supra).

Phytochrome-associated fiber elongation could occur because of phytochrome-mediated plant hormone signaling (Neff et al. 2000. *Genes Dev.* 3:257-271; Colon-Carmona et al. 2000. *Plant Physiol.* 124(4):1728-1738; Stamm and Kumar. 2010. *J. Exp. Bot.* 61(11):2889-2903) such as auxin (IAA), abscisic acid (ABA), gibberellic acid (GA), brassinosteroids (BR), ethylene and cytokinin, which are recognized as key factors associated with fiber development (Lee et al. 2007. *Ann. Bot.* 100:1391-1401). For instance, recent efforts on spatiotemporal manipulation of auxin biosynthesis in developing cotton ovules demonstrated enhancement of fiber yield and quality parameters of cotton (Zhang et al. 2011. *Nature Biotechnol.* 29(5):453-458). There is well-supported evidence on molecular cross-talk between auxin and light signaling, through intimate auxin-phytochrome interaction, in particular PHYA (Neff et al. 2000, supra; Colon-Carmona et al., supra). This could explain fiber quality improvement in our RNAi plants and suggests a role of PHYA gene in this process. Furthermore, through characterization of small RNA species from developing ovules (Abdurakhmonov et al. 2008. *BMC Plant Biol.* 8:93; Devor et al. 2009. *Int. J. Plant Genomics*. PubMedID: 19551152), we observed that photomorphogenesis-related factors (PHYC, SPA1, FAR1, COP1/9, CIP7/8 and RTP2), that are responsible for far red/red light perception and light signal transduction, phototropism, gravitropism and circadian rhythms were targeted by ovule-derived siRNAs at the fiber initiation phase, and more pronouncedly, at the fiber elongation phase of fiber development.

It should be mentioned, however, that we observed a variable trend of fiber trait improvement in $T_2$ RNAi plants from different transformation events, thus suggesting that variable types and levels of RNAi were induced by the PHYA1 gene sequence fragment that we used. This result could be associated with RNAi due to a combination of the different levels of phytochrome gene suppression and the different copy numbers of the RNAi construct in the genome. Our results suggest that two markedly distinct single seed decent RNAi cotton families with specific RNAi phenotypes differ on the copy number of the RNAi plasmid inserted in their genomes as well as the gene-knockout level and suppression of gene combinations. We observed that the three copy number sample was associated with a deeper suppression of the PHYA1 gene. As we proposed, our PHYA1 sequence-based RNAi construct primarily targeted only the cotton PHYA1 sequences and did not affect the other cotton phytochrome genes, not even the PHYA2 genes which have 87% nucleotide identity in both RNAi families selected. However, in $T_3$-31_10, we observed a 10% suppression of cotton PHYB genes that shared ~60% nucleotide identity with the PHYA1 RNAi fragment. These results support our hypothesis that different combinations of phytochrome genes are suppressed with the PHYA1 gene sequence that we used in our transformation. In addition to PHYA1 knock-out, a slight suppression of PHYB in $T_3$-31_10 resulted in early flowering phenotype compared to $T_3$-1_7.

At the same time, the ~2 to 20-fold increases of expression levels of the other phytochrome genes, i.e., PHYA2, PHYB, PHYC, and PHYE, in PHYA1-suppressed RNAi plants were unanticipated results. Interestingly, deeper suppression of the PHYA1 in $T_3$-1_7 resulted in greater expression of the other phytochromes than in the $T_3$-31_10 event. This finding generally agrees with a report of possible overlapping functions of phytochromes genes (Reed et al. 1994. *Plant Physiol.* 1104:1139-1149). In other words, phytochromes can substitute for each other in the regulation of some phytochrome-associated phenotypes such as flowering. Increased levels of PHYA2 and PHYC in the PHYA1 RNAi families can be the result of such a substitution because in rice plants PHYC responds to constant far red light, as PHYA does (Takano et al. 2005. *Plant Cell* 17:3311-3325; Kneissl et al. 2008. *Mol. Plant.* 1(1):84-102) although the photosensory specificity of PHYC is similar to that of PHYB/D/E (Monte et al., supra), which is a weak red-light sensor (Schepens et al. 2004. *Curr. Opin. Plant Biol.* 7(5): 564-569). Additionally, an observed ~5 to 20-fold increase in expression of PHYE/B genes in our PHYA1 RNAi plants suggests a possible overlapping of functions between cotton PHYAs and PHYE/Bs that may be specific for cotton phytochrome species.

We hypothesized that the suppression of PHYA genes in cotton would generate later flowering phenotypes because PHYA generally promotes flowering in plants (Neff and Chory 1998, supra). Alternatively, the increased expression of PHYA2 maintained the early flowering in our selected RNAi cotton families. Also, the increased PHYC expression could contribute to early flowering phenotype in the background of PHYA1 suppression because PHYC is able to promote flowering in the absence of PHYA under long day conditions (Franklin et al. 2003, supra; Monte et al., supra; Balasubramanian et al., supra). This altered expression level of phytochrome genes in RNAi plants might have induced the 'shade avoidance' process, resulting in accelerated plant growth. Plants try to complete their life cycle when shading becomes a problem and accelerate flowering as a response to canopy (Devlin et al. 1999, supra; Salter et al. 2003. *Nature* 426(6967):680-683). We observed elongated leaf petioles and fruiting branches as a marker phenotype in PHYA1 and PHYA1/B RNAi cotton plants, suggesting induction of the shade avoidance process as an attempt to overgrow neighboring plants (Salter et al., supra). Early maturation of cotton bolls observed in PHYA1 RNAi cotton plants could also be associated with response to shade, much as the shade avoidance response in *Arabidopsis* includes both early flowering and early production of seeds (Devlin et al. 1999, supra; Salter et al., supra).

It is noteworthy to mention that there is decreased lint percentage, seed and lint index traits observed in the RNAi families, given that there is a known negative correlation between fiber length and these traits in cotton (Miller and Rawlings. 1967. *Crop Sci.* 7:637-640; Meredith and Bridge. 1973. *Crop Sci.* 13:698-701), leading to overall cotton yield being affected. However, the increased yield potential that we observed in the RNAi plants can be explained by the phytochrome-associated vigorous shoot and root development that produced more fruiting branches, flowers and bolls, which increased the efficiency in assimilation of nutrients from the soil and thus potentially contributed to the observed yield increase. Previous studies showed that overexpression of *Arabidopsis* PHYB gene in potato resulted in higher photosynthetic performance and that transgenic potato plants with increased anthocyanin pigmentation produced increased biomass and increased tuber yield compared to controls (Thiele et al. 1999. *Plant Physiol.* 120(1): 73-82), another possibility is that changed photosynthetic light perception due to altered expression of phytochrome genes, especially increase of PHYB/E and PHYC expression, might have affected the photosynthetic rate, thus leading to the increased yield potential of RNAi plants. Being a red light photosensor, like PHYB, a several-fold overexpression of cotton PHYE/C in PHYA1/B RNAi background could possibly also generate the above-mentioned PHYB overexpressed potato plant phenotype with increased yield potential and anthocyanin pigmentation in PHYA1 RNAi plant senescence.

We are also evaluating improvement in drought-, salt-, cold/freezing-resistance characteristics of developed PHYA1/B RNAi plants due to the observed vigorous root development because previous studies have reported the association of phytochrome genes with these effects (Jonassen et al., supra; Lillo, supra; Datta et al. 2007, supra; Datta et al. 2008, supra; Kim et al., supra; Franklin and Whitelam, supra; Beck et al., supra). Toward this goal, the research and extensive efforts of evaluation of higher generation of these transgenic plants in the natural field conditions as well as stressed environment are in progress.

We used Coker 312, a line with poor yield potential, because of its well-documented high somatic embryogenesis and regeneration efficiency in vitro. The crosses of the transgenic Coker 312 lines with improved cultivars demonstrated the transfer of the same phenotypic and genetic effects from RNAi Coker 312. The simultaneous improvement of several complex traits without affecting other parameters, as we have achieved here through PHYA1 RNAi, is limited in conventional breeding. For example, introgression of fine fiber quality genes from Pima cotton to Upland cotton cultivars using inter-species genetic hybridization is challenging due to wide genetic segregation, linkage drag and genetic distortion in consequent hybrid generations, often resulting in hybrids that are late-maturing and of poor agronomic quality (Endrizzi et al. 1985. *Adv. Genetics* 23:271-375). Our RNAi research results address these fundamental problems and allow for the rapid development of early-maturing cultivars having improved fiber quality, for example, early-maturing Upland varieties having increased fiber quality. Thus, we have developed superior Uzbek cotton cultivars which are adapted for local cotton production while maintaining all other characteristics specific to original cultivar. New markets for longer and stronger cotton lint fiber as well as early maturity and increased yield potential would increase the estimated economic value of the technology. Improvement of resistance to abiotic stresses via phytochrome RNAi further adds to its commercial potential.

Our results support and highlight the importance of plant photomorphogenesis in cotton fiber development and its effect on fiber quality. We conclude that RNAi of cotton PHYA1 genes results in the suppression of targeted genes and also alters the expression level of remaining phytochromes. Observed RNAi effects in cotton, therefore, are due to both the suppression of PHYA1 and the several fold increases in the expression of other phytochromes. This alteration in the cotton phytochrome gene family expression profile results in a changed plant architecture with elongated leaf petioles and fruit branches, early flowering, early boll maturity, enhanced fiber quality and fiber yield phenotypes. These changes are stably expressed in subsequent generations and transferable from the transformed Coker 312 genotype to Upland cultivar through genetic hybridization and selection. Therefore, the development of superior quality long-fibered RNAi cotton plants, based on RNAi of *Gossypium*-derived phytochrome genes, will allow breeders to rapidly improve maturity, major fiber quality traits and yield. Transferred PHYA1 RNAi construct could result in resistance to abiotic stresses in Upland cultivar. This RNAi strategy not only provides a solution to fundamental problems of conventional cotton breeding, but will also result in significant economic income from cotton production worldwide and will open a new paradigm for Upland cotton breeding.

In a preferred embodiment of the present invention, a host cell containing the nucleotide sequences of the invention is a bacterial cell, in particular, an *Agrobacterium tumefaciens* cell.

For both direct gene transfer and *Agrobacterium*-mediated transfer, transformation is usually (but not necessarily)

undertaken with a selectable marker which may provide resistance to an antibiotic (kanamycin, hygromycin or methatrexate) or a herbicide (sulfonylurea, imidazolinone, or basta). The choice of selectable marker is not, however, critical to the invention.

As used herein, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single- or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

As used herein, "recombinant" refers to a nucleic acid molecule which has been obtained by manipulation of genetic material using restriction enzymes, ligases, and similar genetic engineering techniques as described by, for example, Sambrook et al. 1989. Molecular Cloning: A Laboratory Manual, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the term "chimeric" refers to two or more DNA molecules which are derived from different sources, strains, or species, which do not recombine under natural conditions, or to two or more DNA molecules from the same species, which are linked in a manner that does not occur in the native genome. A "construct" or "chimeric gene construct" refers to a nucleic acid sequence encoding a protein, operably linked to a promoter and/or other regulatory sequences.

As used herein, the term "express" or "expression" is defined to mean transcription alone. "Altered levels" or "altered expression" refers to the production of gene product(s) in transgenic organisms in amounts or proportions that differ from that of normal or non-transformed organisms.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences here may include promoters: T7 promoter, CaMV 35S promoter and sub-genomic promoters (two, on either side of the MCS), translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg. 1989. *Biochemistry of Plants* 15:1-82. It is further recognized that since in most cases the exact boundaries of regulatory sequences have not been completely defined, nucleic acid fragments of different lengths may have identical promoter activity.

"RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to a DNA that is complementary to and derived from an mRNA template. The cDNA can be single-stranded or converted to double stranded form using, for example, the Klenow fragment of DNA polymerase I. "Sense" RNA refers to an RNA transcript that includes the mRNA and so can be translated into a polypeptide by the cell. "Antisense", when used in the context of a particular nucleotide sequence, refers to the complementary strand of the reference transcription product. "Antisense RNA" refers to an RNA transcript that is complementary to all or part of a target primary transcript or mRNA and that blocks the expression of a target gene. The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

"Gene suppression" means any of the well-known methods for suppressing expression of protein from a gene including anti-sense suppression or RNAi suppression. In suppressing genes to provide plants with a desirable phenotype, anti-sense and RNAi gene suppression methods are preferred. For a description of anti-sense regulation of gene expression in plant cells see U.S. Pat. No. 5,107,065. For a description of RNAi gene suppression in plants by transcription of dsRNA, see U.S. Pat. No. 6,506,559, U.S. Patent Application Publication No. 2002/0168707 A1 and U.S. patent application Ser. No. 09/423,143 (see WO 98/53083), Ser. No. 09/127,735 (see WO 99/53050) Ser. No. 09/084,942 (see WO 99/61631), all of which are hereby incorporated by reference. Suppression of a gene by RNAi can be achieved using a recombinant DNA construct having a promoter operably linked to a DNA element comprising a sense and anti-sense element of a segment of genomic DNA of the gene, e.g., a segment of at least about 23 nucleotides, more preferably about 50 to 200 nucleotides where the sense and anti-sense DNA components can be directly linked or joined by an intron or artificial DNA segment that can form a loop when the transcribed RNA hybridizes to form a hairpin structure.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. 1987. *Meth. Enzymol.* 143:277) and particle-accelerated or "gene gun" transformation technology (Klein et al. 1987. *Nature (London)* 327:70-73; U.S. Pat. No. 4,945,050, incorporated herein by reference). Additional transformation methods are disclosed below. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. 1985. Supp. 1987. *Cloning Vectors: A Laboratory Manual*; Weissbach and Weissbach. 1989. *Methods for Plant Molecular Biology*, Academic Press, New York; and Flevin et al. 1990. *Plant Molecular Biology Manual*, Kluwer Academic Publishers, Boston. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A "protein" or "polypeptide" is a chain of amino acids arranged in a specific order determined by the coding sequence in a polynucleotide encoding the polypeptide. Each protein or polypeptide has a unique function.

The invention includes functional polypeptides and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. Functional fragments, for example, can vary in size from a polypeptide fragment as small as an epitope capable of binding an antibody molecule, to a large polypeptide capable of participating in the characteristic induction or programming of phenotypic changes within a cell.

A heterologous coding sequence refers to coding sequences which encode peptides or proteins, unrelated to, or, other than, the polypeptides provided above and which are not intrinsically found in the position provided in the chimeric gene construct.

The phytochrome genes PHYA, PHYB, PHYC, PHYD, and PHYE encoding the phytochrome proteins PHYA, PHYB, PHYC, PHYD, and PHYE can be cloned using a variety of techniques according to the invention. The simplest procedure for the cloning of such genes requires the cloning of complementary DNA from viral genomic RNA, or of genomic DNA from an organism identified as producing said protein(s), and the transfer of the cloned DNA on a suitable plasmid or vector to a host organism which does not produce the protein, followed by the identification of transformed hosts to which the ability to produce the protein has been conferred. The transforming protein function—conferring DNA can be cleaved into smaller fragments and the smallest which maintains the protein function—conferring ability can be further characterized. Techniques suitable for cloning by homology include standard library screening by DNA hybridization or polymerase chain reaction (PCR) amplification using primers derived from conserved sequences. As defined herein, two DNA sequences are substantially homologous when at least 80% (preferably at least 85% and most preferably 90%) of the nucleotides match over the defined length of the sequence using algorithms such as CLUSTAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode PHYA1 polypeptides and which hybridize under stringent conditions to the sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Unless otherwise indicated, sequence alignments and percent identity calculations were performed using the Megalign program of the LASERGENE bioinformatics computing suite (DNASTAR Inc., Madison, Wis.), or any equivalent program. Multiple alignment of the sequences was performed using the Clustal W method of alignment (Higgins and Sharp (1989. *CABIOS* 5:151-153) with the default parameters (GAP PENALTY=10, GAP LENGTH PENALTY=1.0), while default parameters for pairwise alignments using the Clustal W method were GAP PENALTY=10, GAP LENGTH PENALTY=1.0, Slow-Accurate unless otherwise indicated.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence, PHYA1. Accordingly, the instant invention comprises the complete sequences as reported in the accompanying Sequence Listing, as well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have PHYA1 protein-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the PHYA1 polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein. Such variants may result from, for example, genetic polymorphism or from human manipulation. Biologically active variants of a native PHYA1 protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even one amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired PHYA1 activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of PHYA1 protein can be observed.

It is to be understood that as used herein the term "transgenic" includes any cell, cell line, callus, tissue, plant part, or plant the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "cotton" as used herein includes any species of the genus *Gossypium* which is used for commercial fiber production, preferably *G. hirsutum* or *G. barbadense*.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, stems, fruits, leaves, roots originating in transgenic plants or their progeny previously transformed with a DNA molecule of the invention and therefore consisting at least in part of transgenic cells, are also an object of the present invention.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants.

EXAMPLES

Having now generally described this invention, the same will be better understood by reference to certain specific examples, which are included herein only to further illustrate the invention and are not intended to limit the scope of the invention as defined by the claims.

Example 1

Plant Material

Plant materials used here in this study were the somatically regenerable cotton genotype *Gossypium hirsutum* line Coker 312 and its transgenic derivative lines, transformed with pHellsgate-8::PHYA1 vector. Regenerable Coker-312 seeds (provided by Dr. Keerti Rathore, Texas A&M University, College Station, Texas, USA). To check the transferability of the RNAi effects observed, we used several commercially important Uzbek cotton cultivars, e.g., *G. hirsutum* cv. AN-Boyovut-2 for the conventional genetic hybridization experiments with RNAi Coker-312 plants.

Example 2

RNAi Vector Construction

We constructed a PHYA1 gene-specific RNAi binary vector construct using high-throughput pHellsgate-8 Gate-Way plasmid vectors (provided by Dr. P. Waterhouse and Dr. C. Helliwell, CSIRO, Australia) (Wesley et al., supra; Helliwell et al., supra). RNAi vectors were transformed into the *A. tumefaciens* strain LBA4404 and used for plant transformation experiments.

For the attB site (attB1 and attB2) of the cotton PHYA1 gene, the attached gene-specific primers, Gos_PHYA1attB1-F and Gos_PHYA1attB2-R (Table 1) were designed and purchased from Integrated DNA Technologies Inc. (Iowa, USA). These primer pairs specifically amplified the 213 bp PHYA1 gene fragment (SEQ ID NO:1) of cotton which corresponds to a portion of the hinge region of the cotton phytochrome A genes. It is noteworthy to mention that tetraploid cottons have two different PHYA1 gene, one acquired from the diploid D-genome ancestor and the other, from the diploid A genome ancestor (Abdurakhmonov et al. 2010, supra). These two PHYA1 genes have 99% nucleotide identity in the 213 bp RNAi portion; they differ by two single nucleotide polymorphisms at the Y (C or T) and R (G or A) positions in the sequence provided and identified by SEQ ID NO:1. First, the specific cotton phytochrome gene fragment for PHYA1 was amplified from cotton genomic DNA with KODHiFi, the high fidelity proof reading DNA polymerase (Novagen, USA) using non attB gene-specific primers according to manufacturer's instructions and protocol. The expected gene-specific PCR products were verified using agarose gel electrophoresis. The attB1 and attB2 sites were then attached to the obtained PCR products, in a second round PCR reaction with attB-flanked gene-specific primers (Table 1) with the purified first PCR-amplicon serving as a template. Size and correctness of obtained attB-flanked PCR products were verified using gel electrophoresis. PCR products were purified with polyethylene glycol (PEG)-solution (containing 26% PEG 8000, 6.5 mM $MgCl_2$ and 0.6 mM sodium acetate pH 5.2) to remove the remaining attB primers. The site-specific recombination reaction with the attB site-flanked gene product and the vector were conducted as described by Helliwell et al. (supra).

The recombination reactions with pDONOR221 (Invitrogen, USA) were carried out in a total volume of 10 μl reaction mixture, with 2 μl BP clonase buffer (Invitrogen, USA), 2 μl attB site flanked PCR product, 150 ng plasmid vector and 2 μl BP clonase (Invitrogen, USA). The reaction mix was incubated at 25° C. overnight. The recombination mix (2 μl) was transformed into chemically-competent DH5-alpha *E. coli* cells (Invitrogen, USA). Transformed cells were grown in LB (Lysogene Broth) plates containing 50 mg/L spectinomycin. Colonies were subjected to further plasmid isolation and analyzed for insertions by PCR using M13 primers. Plasmids were isolated by the NaOH/SDS lysis method (Sambrook et al., supra). The recombination reaction from pDONOR221 plasmid containing the attB-PHYA1 insert into pHellsgate-8 was conducted in a total volume of 10 μl, with 2 μl LR clonase buffer (Invitrogen, USA), 2 μl recombinant pDONOR221-attB-PHYA1 (150 ng), 300 ng pHellsgate-8 and 2 μl LR clonase (Invitrogen, USA), following manufacturer's instructions. The reaction mix was incubated overnight at room temperature, treated with proteinase K and 2 μl of the aliquot was transformed into DH5-cells (Invitrogen, USA). Cells were grown in LB-plates containing the selective antibiotic spectinomycin. Colonies were picked for further verification of correct recombination with attB-sites. Restriction analyses with XhoI (for sense orientation) and Xba (anti-sense orientation) were carried out; verified clones were selected for further RNAi vector preparation, as described by Helliwell et al. (supra).

TABLE 1

Primer pairs and probes for PCR-amplification, vector construction and quantitative real-time PCR.II

| Name | Sequence (5'-3') | # (nt) | SEQ ID NO: | Amplicon Size (bp) | Ref. |
|---|---|---|---|---|---|
| Gos_PHYA1attB1-F* | GGGGACAAGTTTGTACAA AAAAGCAGGCTGTGCTCG GAGTTAGTCCCATCAC | 52 | 3 | 270 | This study |
| Gos_PHYA1attB2-R* | GGGACCACTTTGTACAAG AAAGCTGGGTGTCCGTAT GATTGTTGATTGTCG | 51 | 4 | 270 | |

TABLE 1-continued

Primer pairs and probes for PCR-amplification, vector construction and quantitative real-time PCR.II

| Name | Sequence (5'-3') | # (nt) | SEQ ID NO: | Amplicon Size (bp) | Ref. |
|---|---|---|---|---|---|
| 35S-F | GTTCATTTCATTTGGAGAGG | 20 | 5 | 500 | This study |
| PDK-R | CGTCTTACACATCACTTGTC | 20 | 6 | | |
| PDK-F | CTTACATTTGGATTGATTACAG | 22 | 7 | 358 | This study |
| OST-R | CGCATATCTCATTAAAGCAG | 20 | 8 | | |
| nptII-F | GATAGCGGTCCGCCACAC | 18 | 9 | 113 | Yi et al. 2008 |
| nptII-P | 6FAM-TTTCCACCATGATATTCGGCAAGCAGG-TMR | 27 | 10 | | |
| nptII-R | CGAGGATCTCGTCGTGACACAT | 22 | 11 | | |
| UBC1-F | TGGCATTATATTGTCATTGTTACTATCC | 28 | 12 | 121 | Yi et al. 2008 |
| UBC1-P | 6VIC-CTTAAATTTCCAAGCAGCAGAAGCCTMR | 28 | 13 | | |
| UBC1-R | ACCATGTTATCTTATTCTAAGACAAGCTC | 29 | 14 | | |
| PHYA1_ex1&2-qRT_F | GTTGTCCTTGGCATTGCAG | 19 | 15 | 132 | This study |
| PHYA1_ex1&2-qRT_R | TTTTCATGGAGATCCCGGTTC | 21 | 16 | | |
| PHYA2_ex3&4-qRT_F | GTTCACCTTGCACATTTGGAG | 21 | 17 | 179 | This study |
| PHYA2_ex3&4-qRT_R | CCTGCTTCCCTCAAGTACTG | 20 | 18 | | |
| PHYB1_and2_qRT-F | TGCAGAATTAACAGGACTCTCAG | 23 | 19 | 213 | This study |
| PHYB1_and2_qRT-R | TTACTAGAGCAAGCGTTCACC | 21 | 20 | | |
| PHYC_hinge_qRT-F | AGCTCAACCATTAAGTCTCTGTG | 23 | 21 | 145 | This study |
| PHYC_hinge_qRT-R | TTGCTCACTGTCCATCTCATC | 21 | 22 | | |
| PHYE_hinge_qRT-F | GCCATGCAAATCCGGTTAAG | 20 | 23 | 149 | This study |
| PHYE_hinge_qRT-R | AACGACTGCCATCACTAACG | 20 | 24 | | |
| GhPP2A1_F | GATCCTTGTGGAGGAGTGGA | 20 | 25 | 100 | Artico et al. 2010 |
| GhPP2A1_R | GCGAAACAGTTCGACGAGAT | 20 | 26 | | |

TABLE 1-continued

Primer pairs and probes for PCR-amplification, vector construction and quantitative real-time PCR.II

| Name | Sequence (5'-3') | # (nt) | SEQ ID NO: | Amplicon Size (bp) | Ref. |
|---|---|---|---|---|---|
| A1341-F | GCATGCTGAATTGACAGAACCAGCY | 25 | 27 | 681 | Cronn et al. 2002 |
| A1341-R | CACTCACAAAGTTATGCCGGATGY | 24 | 28 | 681 | |

*attB1 and attB2 sequences are underlined

Example 3

Cotton Transformation and Somatic Embryogenesis

For cotton transformation and somatic embryogenesis, we used the methodology of Sunilkumar and Rathore (2001. Mol. Breeding. 8:37-52) modified with regard to the plant regeneration medium based on other tissue culture studies in cotton (Stewart and Hsu. 1977. Planta 137:113-117; Firoozabady et al. 1987. Plant Mol. Biol. 10:105-116). All reagents for cotton tissue culture were purchased from Phytotechnology Laboratories®, USA. The $T_0$ plantlets were transferred into soil in pots and grown in a greenhouse environment in 2008.

Sulfuric acid delinted cottonseeds of Coker-312 were surface sterilized in 10 minute wash with 70% ethanol and briefly burned under the hood to remove the ethanol traces. Seeds were planted into 0.7% agar medium and kept under the dark condition for 3 days at 28° C. for germination. Germinated seeds were placed under a photoperiodic condition of 16 hours light followed by 8 hours dark for the development of seedlings. Hypocotyl sections of 5-7 mm were isolated from one-week old seedlings. From these hypocotyl sections, 75% were used for transformation experiments; the remaining 25% of the sections were kept separate as a negative control. The hypocotyl sections were wounded with a laboratory razor in several places and placed on medium P1 [4.31 g/L MS salt, 0.4 mg/L thiamine HCL, 100 mg/L myoinositol, 0.75 mg/L $MgCl_2$, 3% glucose, 0.2% Phytagel, 5 mg/L 2 ip, 0.1 mg/L NAA, pH 5.8]. LBA4404 suspension (5 µl), bearing pHellsgate-8::PHYA1 RNAi vector, was applied onto the wounded hypocotyl sections and then incubated in the dark at 22° C. for 72 hours. The pHellsgate-8::PHYA1 RNAi vector was grown in YEP medium [10 g/L Bacto peptone, 5 g/L NaCl, 10 g/L Bacto yeast extract, pH 7.0] containing rifampicin (10 m/L) and spectinomycin (50 mg/L) antibiotics. Bacterial cultures were grown in tubes for 36 h at 26° C. with 200 rpm shaking. Cells from 5 tubes were pooled, harvested by centrifugation, and resuspended in 10 ml of pre-induction medium (10 g/L glucose, 14.62 g/L MES, 20 ml/L sodium phosphate buffer pH 5.6, 50 ml/L 20×AB salt stock (Chilton et al. 1974. Proc. Nat. Acad. Sci. USA 71(9):3672-3676) containing 100 µM acetosyringone. For controls, 5 µl sterile water was applied in place of bacterial suspension.

After 72 hours, infected and control hypocotyl sections were transferred to fresh P1 medium, containing kanamycin (50 mg/L) and cephabol (500 mg/L; analog of clavamox) and cultures were grown under a 16 h photoperiod (10 µmol m-2 s-1). After three weeks, 3 mm callus tissues grown in selective P1 medium were transferred into new P7 medium [4.31 g/L MS salts, 0.4 mg/L thiamine HCL, 100 mg/L myo-inositol, 0.75 mg/L MgCl, 3% glucose, 0.2% Phytagel, 0.1 mg/L 2ip, 5 mg/L NAA, pH 5.8] and grown in continuous culture, sub-culturing the tissues each month. Callus tissues with less than 3 mm were kept in P1 medium for another three weeks and subsequently transferred to the P7 medium. After 16 weeks of somatic embryogenesis induction, callus tissues grown on selective P7 medium were transferred to new modified medium R5, containing 4.31 g/L MS salt, 1 ml/L vitamins Gamborg solution, 1.9 g/L $KNO_3$, 0.75 mg/L MgCl, 3% maltose, 0.2% Phytagel). The somatic embryos were generated in 12-16 weeks in R5 medium. The somatic embryos of 6-7 mm size were then transferred into modified SH1 medium [10 ml/L 100× micronutrients, 50 ml/L 50× macronutrients, 1 ml/L vitamin B5, 5 g/L sucrose, 15 g/L bactoagar, 2 g/L phytogel] medium and incubated at dark condition for 10 days. A desiccation and root initiation process occurred during this time period. Embryos were then transferred to new SH-2 medium [10 ml/L 100× micronutrients, 50 ml/L 50× macronutrients, 1 ml/L vitamin B5, 20 g/L sucrose, 1 g/L Phytagel, and 5 g/L agar] and grown for 10 days under a 16 h photoperiod (10 µmol m-2 s-1) for the development of roots and leaves. After the development of initial roots and leaves, embryo plantlets were transferred to SH-3 medium [10 ml/L 100× micronutrients, 50 ml/L 50× macronutrients, 1 ml/L vitamin B5, 20 g/L sucrose, 1 g/L Phytagel and 2.25 g/L agar] and grown in increased light (70 µmol m-2 s-1) for full development of roots and leaves. After 10 days, fully developed embryo plantlets were transferred into plastic containers with SH-3 medium resulting in the development of 4-5 leaves and additional roots.

Example 4

Identification of Transformed Plants Using PCR

From each cotton genotype tested, genomic DNAs were isolated from the frozen leaf tissues using method of Dellaporta et al. (1983. Plant Mol. Biol. Rep. 1:19-21) with minor modification and optimization for frozen tissues. Prepared genomic DNAs were analyzed in 0.9% agarose electrophoresis and DNA concentrations were estimated based on Hind III digested λ-phage DNA. RNAi vector-specific 35S-F/PDK-R or PDK-F/OST-R primers pairs (Table 1) were used to verify the positive transgenic plants.

Amplification reactions were performed in 50 µl volumes containing 4.5 µl 10×PCR buffer with $MgCl_2$, 1 µl BSA, 0.5 µl 25 mM of a dATP, dGTP, dTTP, and dCTP mix, 2.5 µl 50 ng/ml of each reverse and forward primer, and 1 µl 50 ng/ml template DNA. Taq DNA polymerase (0.5 U) (Sigma, USA) was added to the reaction at the annealing temperature of first cycle. Amplifications were carried out with a first denaturation at 94° C. for 3 min followed by 45 cycles of 94° C. for 1 min, 55° C. for 1 min (annealing) and 72° C. for 2 min (extension). A final 5-min extension at 72° C. was then performed. For determining PCR-products, 2%-agarose (Sigma) gel-electrophoresis was carried out in 0.5×TBE buffer. Gels were stained with ethidium bromide.

Example 5

RNAi Plant Evaluations $T_0$ and $T_1$ Generations:

PCR-positive, transgenic $T_0$ RNAi Coker 312 plants along with non-transgenic control embryonic plants, both obtained through somatic embryogenesis, were transferred into soil pots and grown in the greenhouse environment to produce self-pollinated $T_1$ seeds. Self-pollination was achieved by wrapping the petals with cotton threads before flower opening. Further, 15-20 $T_1$ seeds from each PCR-positive $T_0$ plants were germinated in small paper-soil pots at the greenhouse environment; then, genomic DNAs were isolated from the small piece of cotyledon leaf tissues and PCR amplification was conducted using RNAi vector specific primers. The, PCR-positive $T_1$ plants were selected for further growing and when the first true leaves appeared, they were transferred into larger pots to perform phenotypic observations and produce self-pollinated $T_2$ seeds. In $T_1$ generation, RNAi plants were evaluated for flowering time and boll maturation as well as fiber staple length characteristics compared to same greenhouse environment grown non-transgenic Coker 312 plants. Flowering time was determined from the first flower opening date and number of opened flowers. Boll maturation was determined based on number of open bolls per $T_1$ plant at the time of evaluations. Fiber length was measured manually and compared to normal Coker 312 fibers.

$T_2$ Generation:

Based on preliminary flowering and fiber characteristics, individual $T_1$ plants from different transformation events, were selected for subsequent $T_2$ generation plant evaluation. For this, 40-45 $T_2$ seeds from each selected PCR-positive, $T_1$ plants were planted, germinated in small paper-soil pots under solar light conditions. When true leaves appeared, they were transplanted into the field station of the Institute of Genetics and Plant Experimental Biology, Tashkent, Uzbekistan in 2009. Forty to 45 $T_2$ plants, derived from each $T_1$ plant (single seed decent) of different transformation event, were grown as a family with 25 non-transgenic control Coker 312 plants in standard field plot design in a two row (60 cm row spacing) plot 10 meters long. The average indices for hypocotyl length, number of opened flowers and opened bolls of each field-grown $T_2$ RNAi family and control plants were recorded. First flowers opened were tagged with date indication to determine flowering time difference. Fiber quality traits of these field grown individual $T_2$ generation RNAi and control plants, including upper half mean (UHM), fiber strength (STR), micronaire (MIC), and fiber uniformity was measured using High Volume Instrumentation (HVI) at the fiber testing Center "SIFAT", Tashkent Uzbekistan. All plants were self-pollinated to produce pure $T_3$ generation seeds, wrapping the petals with cotton threads before flower opening.

$T_3$ Generation:

Based on field evaluations in 2009, we selected plants from two different $T_2$ RNAi plant families ($T_2$-1_7 and $T_2$-31_10) with improved cotton fiber quality, vigorous shoot and root development and early flowering phenotypes compared to control plants. In 2010, self-pollinated $T_3$ generation seeds from these two RNAi families were grown in the same field conditions in a 10 m row, 10 meter long plot (90 cm row spacing, 0.010 ha), along with side-by-side grown 0.010 ha control plants. We measured yield by weighing the seed cotton from 600 hundred plants/0.010 ha of $T_3$ RNAi cotton families and control families. Lint percentage, the weight of 100 seeds (seed index) and lint index were measured manually and averaged from 24 individual plants of each selected $T_3$ RNAi plant families and control plants, taking seed cottons from six fully matured bolls per plant. We individually analyzed fiber quality traits of these $T_3$ generation RNAi family plants at fiber testing Center "SIFAT", Tashkent Uzbekistan. We also measured the root length in these selected RNAi family plants, growing PCR-positive seedlings at the special laboratory plastic pots in greenhouse. Root length was measured after 25 days of seed germination, comparing it to same age Coker 312 control plants from the same growing environment. For this, plastic pots were cut and soil contents around the roots were carefully washed. Additionally, $T_3$ plants from the field were dug at the flowering and boll maturation stages, roots were washed and root lengths were compared with control plants growing in the same field. The statistical significance of trait differences between RNAi families and control plants were tested with nonparametric two paired sample test (Wilcoxon matched-pairs signed-rank test) using Plainstat ver. 0.2.1 (Retrieved from the Internet: <URL:.plainstat.com).

Cotton Transformation and Phenotypic Observations in $T_0$-$T_3$ Generations

We successfully obtained populations of transgenic cotton callus tissues bearing cotton PHYA1 RNAi construct (FIG. 1), which were resistant to the selectable marker, kanamycin. These transgenic callus tissues were grown to the stage of somatic embryos and transgenic embryonic plants were obtained. Compared to somatically regenerated non-transformed controls, we observed a very rapid and vigorous lateral and main root development, a changed plant architecture with elongated petioles and fruiting branches and early flowering phenotype in all candidate-transgenic cotton embryo plants transformed with pHellsgate-8::PHYA1 RNAi vector (FIGS. 1 and 2).

Figure 2:
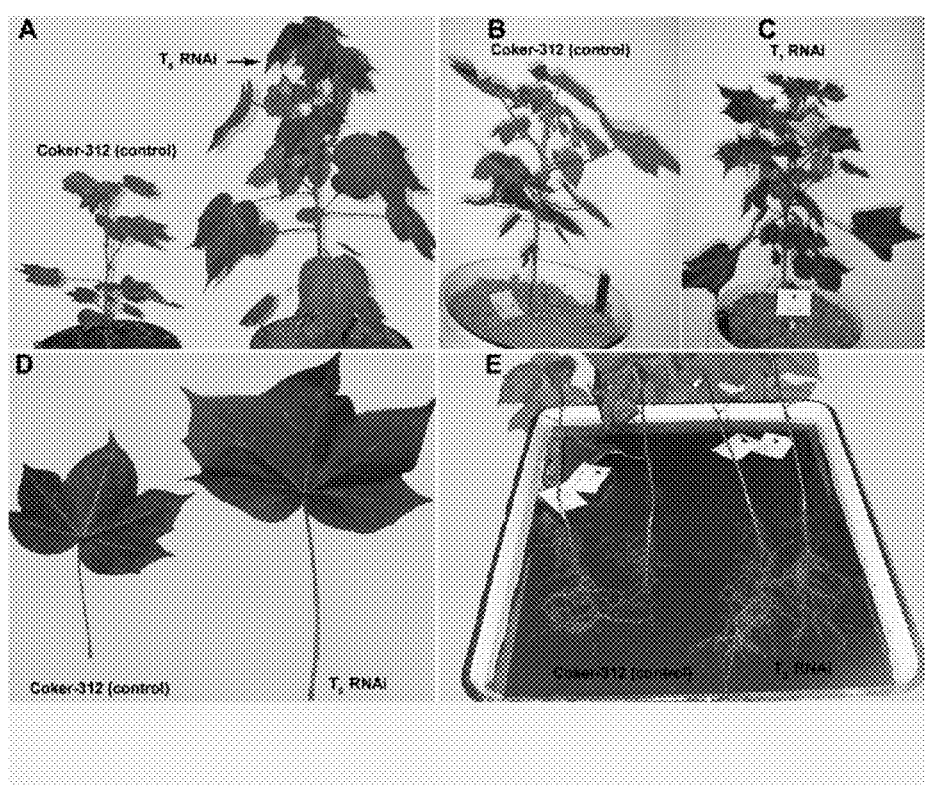
Figure 3:
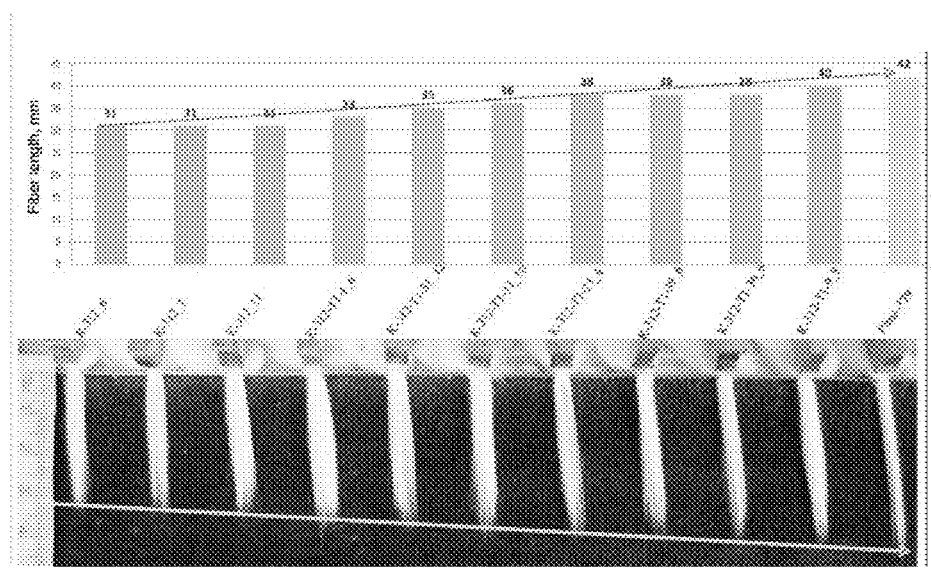
FIG. 3 depicts the staple length of fibers from RNAi cotton plants in $T_1$ generations. Green bars are staple length indices for 3 individual Coker-312 plants (marked as K-312); amber bars are staple length indices from individual $T_1$ generation RNAi plants; and yellow bar is staple length indices for Pima cotton. Control and RNAi Coker-312 plants were grown in the same greenhouse environment.
Figure 4:
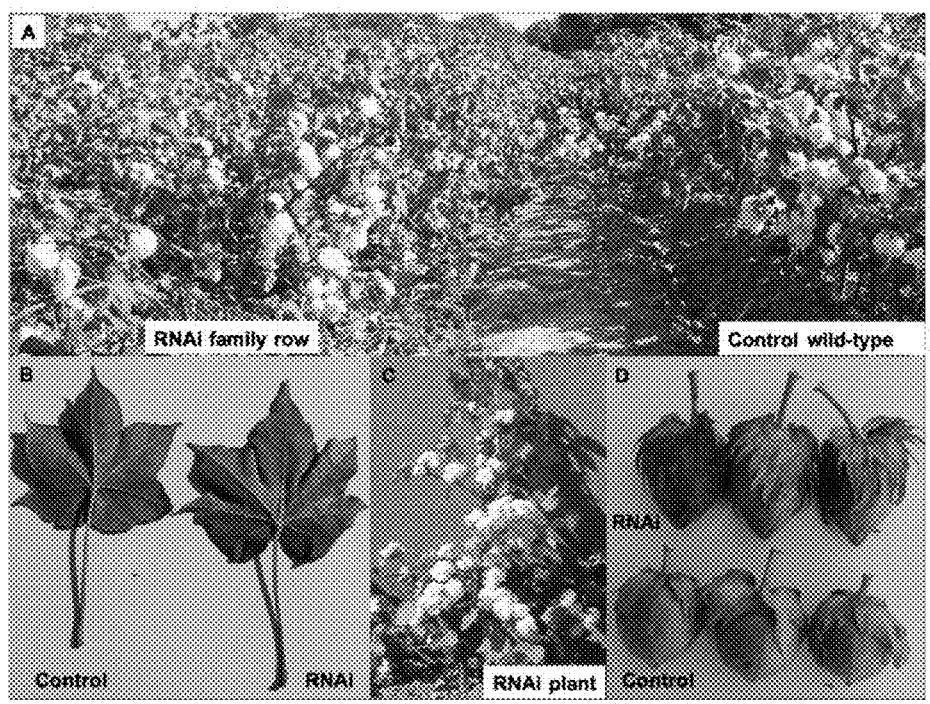
FIGS. 4A-4D show phytochrome-associated RNAi effects in a RNAi line derived from the cross between RNAi Coker 312 and AN-Boyovut-2 (Uzbek variety) cultivar.

When we measured fibers from $T_0$ embryonic plants, fibers of transgenic RNAi plants were, at least, 5 mm longer than fibers on control plants (FIG. 1). PCR-analysis to validate the insertion of the RNAi construct into genomic DNAs of $T_0$ and $T_1$ as well as $T_2$ (data not shown) proved the transformation of RNAi construct and its stable inheritance in subsequent generations. Detailed phenotypic evaluation of field grown plants of $T_1$ and $T_2$ generation RNAi plants also revealed vigorous vegetative growth with markedly changed plant architecture (FIG. 2), 5-10 days earlier flowering and earlier boll maturing phenotypes (FIG. 2) and fiber UHM length increase of 2 mm up to 8 mm FIG. 3. As a marker phenotype, plants with longer hypocotyls and elongated leaf petioles also had more anthocyanin pigmentation in stem and leaves of RNAi plants compared to controls. This pigmentation was markedly expressed in the boll maturation period (FIG. 4).

Figure 5:
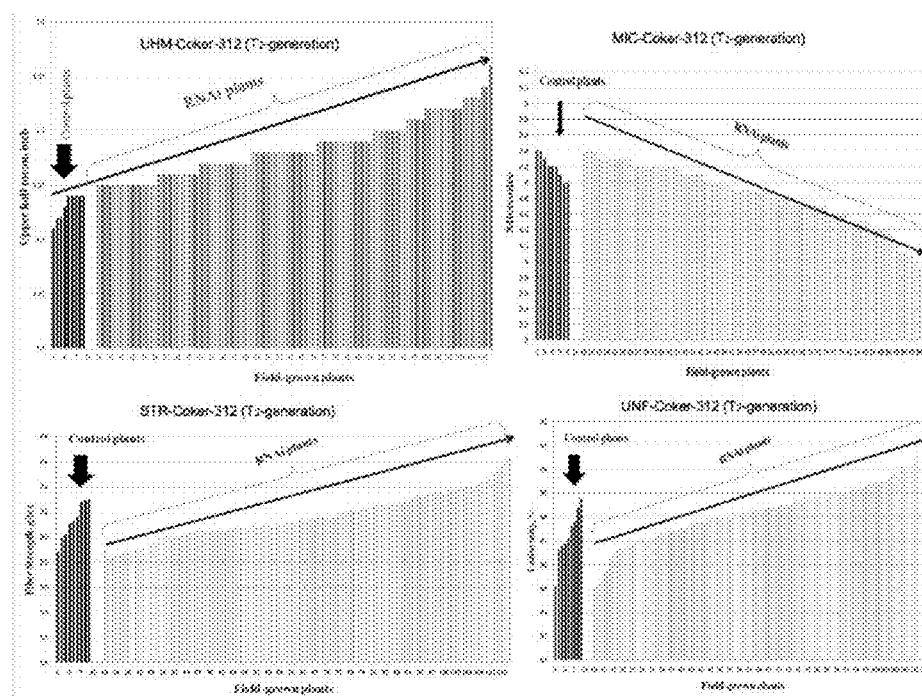
FIG. 5 shows a general trend of changing the major fiber quality traits in second generation RNAi plants of Coker-312, compared to controls grown under the same conditions.

Analysis of major fiber characteristics in $T_{2:3}$-generations
To analyze the fiber characteristics of field-grown $T_2$ plants, we harvested bolls from each individual plant. We selected 89 plants that flowered and matured 5-10 days earlier than non-transformed plants among the different RNAi families and measured the major fiber traits and compared with fibers from 8 individual non-transformed Coker 312 plants grown in the same field side-by-side with RNAi plants under the same growing conditions. HVI analysis of fiber samples revealed that plants containing the pHellsgate-8::PHYA1 RNAi construct, had increased fiber length (upper half mean—UHM) ranging from 1.25 to 1.36 inch (FIG. 5). Generally, other fiber characteristics micronaire (MIC) and fiber uniformity (UI) also were significantly improved (p<0.0001; FIG. 5). For example, we observed high quality individual RNAi genotypes with fiber length of 1.32 inch, micronaire of 4.6, fiber strength of 35.5 g/tex, and fiber uniformity 88%. Non-transformed control Coker-312 plants grown in the same field had an average UHM of 1.23 inch, MIC 5.2, STR 31 g/tex, and UI of 87%.

Figure 6:
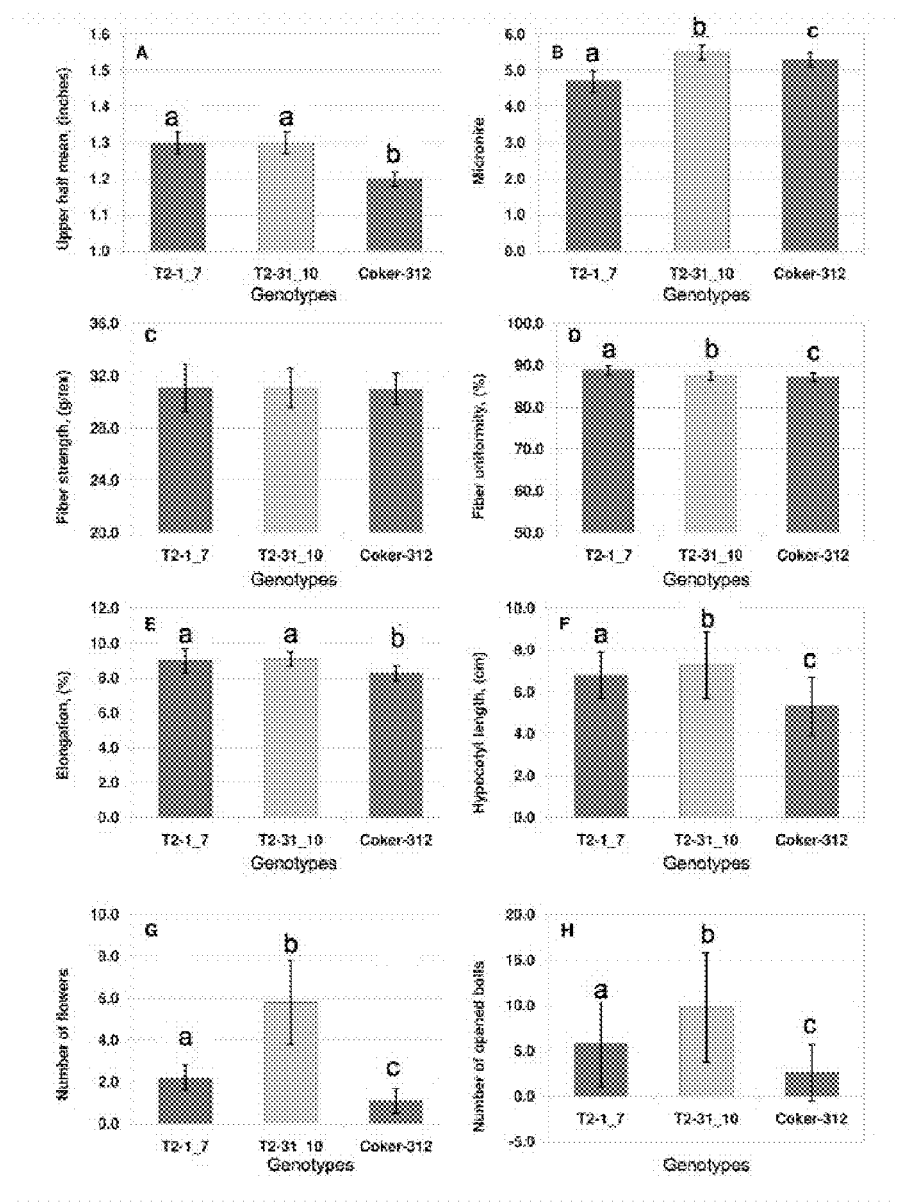
FIGS. 6A-6H depict the histograms for average phenotypic characteristics of selected $T_2$-generation PHYA1 RNAi plant families ($T_2$-1_7 and $T_2$-31_10) compared to the same environment- and condition-grown control cotton plants.
Figure 7:
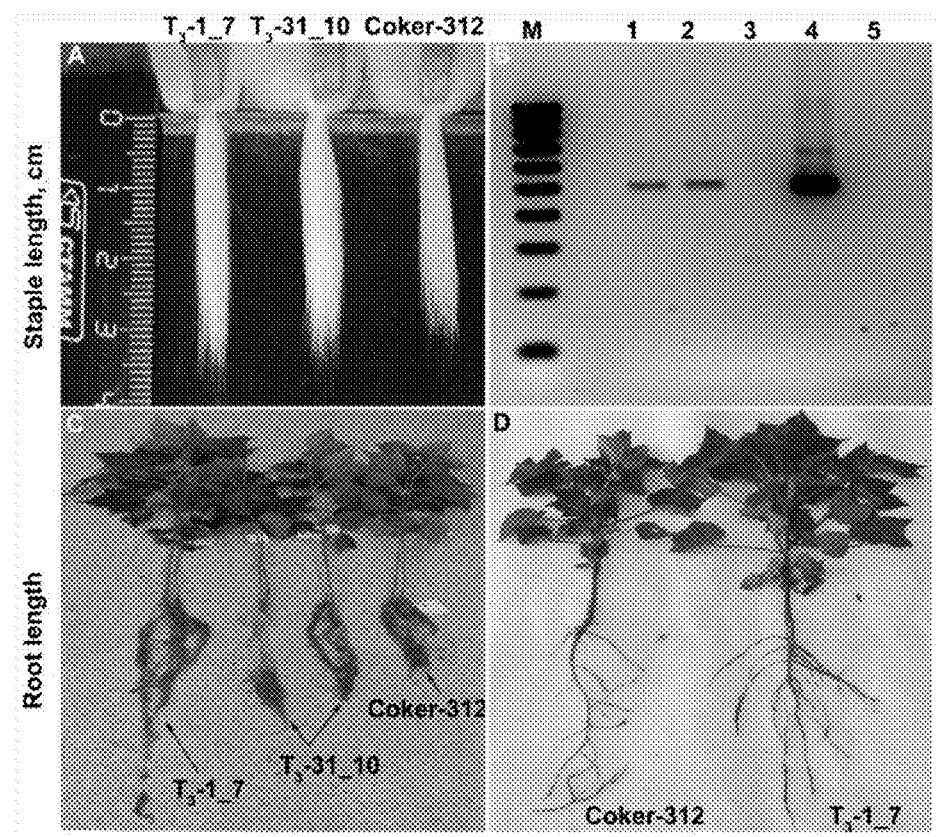
FIG. 7A depicts fiber length characteristics and FIGS. 7C and 7D depict root development characteristics of selected $T_3$-generation PHYA1 RNAi plant families ($T_3$-1_7 and $T_3$-31_10) compared to the same environment- and condition-grown control cotton plants. PCR-verification of these selected plants is shown in FIG. 7B: M-100 bp ladder, 1—$T_3$-1_7; 2—$T_3$-31_10; 3—Coker 312; 4—pHellsgate-8:: PHYA1 plasmid; 5—no DNA template control. These plants were used for copy number identification and relative expression analyses using qPCR.
Figure 8:
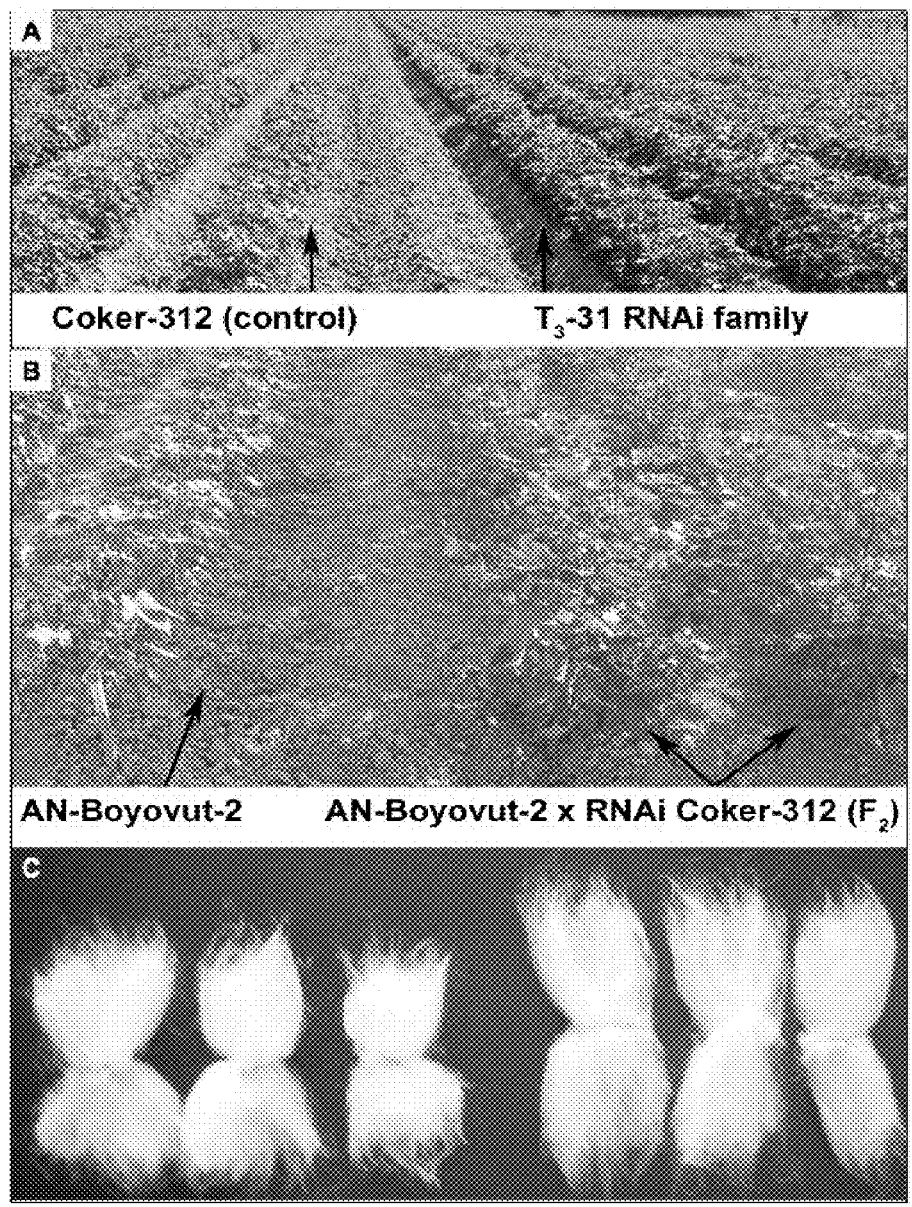
FIGS. 8A and 8B show the difference in vegetative growth between field grown $T_3$ RNAi and control plants in the experimentally controlled field test of 2009 (FIG. 8A). The transferability of the phytochrome-associated RNAi effects from RNAi Coker-312 to Upland cultivar (AN-Boyovut-2) is shown in FIGS. 8A and 8B.
FIG. 8C compares the improvement of fiber samples between the original cultivar (left) and the RNAi $F_2$ hybrids (right) grown in the same environment.

Based on $T_2$ phenotypic evaluation, we selected two plant families, namely $T_2$-1_7 and $T_2$-31_10, with significantly improved fiber quality such as UHM (p<0.001), MIC (p<0.001), UI (p<0.02), ELO (p<0.0001), flowering (p<0.01), hypocotyl length (p<0.0001) and boll maturation (p<0.0001) characteristics compared to the control plants (FIG. 6). In both RNAi families, average fiber length was significantly (p<0.0001) increased; however, $T_2$-1_7 RNAi family plants had significantly improved MIC (p=0.00006) and UI (p=0.001) compared to $T_2$-31_10 family plants. In contrast, $T_2$-31_10 plants had longer hypocotyls (p=0.0001), more opened flowers (by Jul. 15, 2009; p=0.005) and bolls (by Sep. 15, 2009; p<0.0001) compared to $T_2$-1_7 RNAi family. Additionally, we observed longer main and lateral roots in the $T_2$-1_7 RNAi family compared to both the $1_2$-31_10 family and control Coker 312 (FIG. 7). Field evaluations of these two selected RNAi families in 2010 showed that the major RNAi effects observed in $T_{1:2}$ generations is stably expressed in $T_3$, and we observed a consistent improvement in fiber traits such as strength, UHM, UI and ELO (p<0.05) (Table 2, FIG. 7A), root development (FIG. 7C, D) and boll maturity (FIG. 6H) as well as vigorous vegetative growth (FIG. 8). However, in 2010 environment, the observed difference in improvement on MIC of $T_3$-31_10 fiber was not statistically significant than control fiber, but fiber of $T_3$-1_7 RNAi family was significantly different than control fiber. At the same time, in 2010 environment, we observed statistically significant (p≤0.02) improvement on average STR of $T_3$ RNAi plants compared to controls.

The measurement of other fiber characteristics in the selected $T_3$ families showed small, but statistically significant (p<0.05-0.001) decrease up to 1.6% in lint percentage, 3.8% in seed index (weight of 100 seeds) and up to 9.8% decrease in lint index (Table 2). However, up to 6 kg (18%) more seed cotton weight in $T_3$ RNAi families compared to control non-transgenic Coker 312 plants. A summary of results are shown in Table 2.

TABLE 2

Average fiber quality traits for selected $T_3$ generation RNAi plant families and control plants, grown under experimental field conditions in 2010

| Traits | Coker-312 (Control) | $T_3$_1-7 | $T_3$_31-10 |
| --- | --- | --- | --- |
| UHM (SD) | 1.2 (0.02) | 1.3 (0.01)*** | 1.3 (0.02)*** |
| MIC (SD) | 5.6 (0.42) | 5 (0.43)*,a | 5.4 (0.25)a |
| STR (SD) | 28.8 (1.08) | 30.9 (2.06)**,a | 29.7 (0.73)*,a |
| UI (SD) | 87.5 (1.17) | 89.2 (2.01)* | 88.1 (0.95)* |
| ELO (SD) | 9 (0.6) | 10 (0.48)**** | 10.1 (0.56)**** |
| Wgt: 100 seeds (SD) | 12.9 (0.9) | 12.4 (1.3) | 12.4 (0.7)* |
| Lint % (SD) | 38.7 (1.7) | 37.3 (2.1)* | 37.1 (1.9)* |

TABLE 2-continued

Average fiber quality traits for selected $T_3$ generation RNAi plant families and control plants, grown under experimental field conditions in 2010

| Traits | Coker-312 (Control) | $T_3$_1-7 | $T_3$_31-10 |
| --- | --- | --- | --- |
| Seed weight % (SD) | 61.3 (1.7) | 62.7 (2.1)* | 62.9 (1.9)* |
| Lint index (SD) | 8.1 (0.5) | 7.4 (0.9)*** | 7.3 (0.7)*** |

UHM—upper half mean (inches);
MIC—micronaire;
STR—fiber strength (g/tex);
UI—fiber uniformity (%);
ELO—elongation (or fiber elasticity, %);
SD—standard deviations.
*, , *, ****compared to control, statistically significant in Wilcoxon matched-pairs signed-rank test at p ≤ 0.5, p ≤ 0.01, p ≤ 0.005 and p ≤ 0.0001.
Lint index = (Lint % × weight of 100 seeds)/seed weight %.
Statistical significance of measured traits between two RNAi families ($T_3$_1-7 and $T_3$_31-10) in Wilcoxon matched-pairs signed-rank test was shown as $^a$p ≤ 0.05.

Example 6

Copy Number Identification for the Integrated RNAi Vector Sequence

Real-time quantitative PCR was used to identify the copy number of the integrated transgene vector sequence in the $T_3$ generation. For this, we followed the methodology and copy number calculation described by Weng et al. (2004. *Plant Mol. Biol. Rep.* 22:289-300) and utilized the neomycin phosphotransferase II (nptII) and *G. hirsutum* $A_t$-genome specific ubiquitin (GhUBC1) gene-specific primer pairs and Taq Man real-Time PCR probes (Table 1) developed for copy number identification in transgenic cotton lines (Yi et al. 2008. *Anal. Biochem.* 375(1):150-152).

For creation of the standard curve, we cloned GhUBC1 fragment into the plasmid vector pCR4® TOPO-TA following manufacturer's protocol and instructions (Invitrogen, USA); the plasmid vector contains the nptII gene as a selectable marker. Thus, a reference plasmid vector containing both nptII and GhUBC1 gene for constructing a standard curve based on absolute copies of the plasmid vector was obtained. The pCR4-TOPO-nptII-GhUCB1 vector was ~4.1 kb long; therefore, 20 ng of the initial concentration used for the amplification had 4526321921 copies. We made six 10-fold serial dilutions and amplified target genes using qPCR primer pairs and probes (Table 1).

Real-time quantitative PCR was carried out on an Applied Biosystems 7500 real-time PCR systems (Applied Biosystems, Foster city, USA). PCR reactions were performed in 12.5 µl volume with the following standard program recommended by the manufacturer: 95° C. for 10 min, followed by 40 cycles of 95° C. for 15 s and 60° C. for 1 min. Each 12.5 µl reaction mixture contained 6.25 µl Master Mix (2×), 0.25 µl (200 nM) of each primer (10 µM), 1 µl (40 nM) of probe (0.5 µM), 4 µl of template DNA sample (0.2 pg to 20 ng), and 0.75 µl sterile deionized water. 2×PCR Master Mix contained No AmpErase UNG, AmpliTaq Gold DNA polymerase, deoxynucleoside triphosphates with dUTP and Taq Man reaction buffer with magnesium chloride (Applied Biosystems, Foster city, USA).

Average $C_t$ values were plotted against log of absolute copy numbers to obtain standard curves. Six replicate reactions were conducted to construct standard curves for each target gene. Efficiencies of amplification were calculated based on slopes of standard curves with the formula: $E = 10^{(-1/slope)} - 1$ (Ginzinger, 2008; Yi et al., supra). The copy number calculation was performed as described by Weng et al. (supra) with deducing of $X_0/R_0 = 10^{[(Ct, X-IX)/SX)]-[(Ct, R-IR)/SR]}$, where X is nptII, R is UBC1, I is intercept of the standard curve, S is slope of the standard contained 2 copies of pHellsgate-8::PHYA1 RNAi vector in their genomes. As an additional control, we included a DNA sample of Bt-cotton that has single copy of cry I transgene inserted in its genome (Table 4).

TABLE 3

Standard curve for kanamycin (nptII) and ubiquitin (UBC1) genes using pCR4 TOPO nptII-GhUBC1 plasmid vector (4.1 kb)

| DNA ng | Amount copy | Avg Ct values* | SD | SE | CV, (%) | Slope | Intercept | $R^2$ | Efficiency** |
|---|---|---|---|---|---|---|---|---|---|
| | | nptII | | | | −3.42 | 36.6 | 1.0 | 96.00% |
| 20.0 | 4526321921 | 3.93 | 0.18 | 0.07 | 4.6 | | | | |
| 2.0 | 452632192 | 6.48 | 0.17 | 0.08 | 2.6 | | | | |
| 0.20 | 45263219 | 10.47 | 0.17 | 0.07 | 1.6 | | | | |
| 0.02 | 4526322 | 13.85 | 0.44 | 0.18 | 3.3 | | | | |
| 0.0020 | 452632 | 17.01 | 0.51 | 0.21 | 3 | | | | |
| 0.0002 | 45263 | 20.9 | 0.22 | 0.09 | 1.1 | | | | |
| | | GhUBC1 | | | | −3.42 | 36.19 | 1.0 | 96.00% |
| 20.0 | 4526321921 | 3.56 | 0.07 | 0.03 | 2 | | | | |
| 2.0 | 452632192 | 6.2 | 0.27 | 0.12 | 4.4 | | | | |
| 0.20 | 45263219 | 10.1 | 0.16 | 0.07 | 1.6 | | | | |
| 0.02 | 4526322 | 13.29 | 0.25 | 0.1 | 1.9 | | | | |
| 0.0020 | 452632 | 16.37 | 0.32 | 0.14 | 2 | | | | |
| 0.0002 | 45263 | 20.76 | 0.36 | 0.15 | 1.7 | | | | |

SD—standard deviation;
SE—standard error = SD/SQRT(n), where n is sample size.
*qRT-PCR reaction for each dilution was repeated 6-times; average values are shown;
**Efficiency of PCR was calculated using following formula: $E = 10^{(-1/slope)} - 1$ and is presented as percentage.

TABLE 4

Estimated numbers of nptII in third generation ($T_3$) RNAi cotton lines

| Samples | Average Ct values* | SD | SE | CV | $X_0/R_0$ | Estimated copy number | cv* |
|---|---|---|---|---|---|---|---|
| nptII__$T_3$-1__7 | 22.01 | 0.75 | 0.24 | 3.4 | 3.08 | 3 | 0.037 |
| nptII__$T_3$-31__10 | 21.07 | 0.29 | 0.09 | 1.4 | 1.67 | 2 | 0.025 |
| nptII__Bt-cotton | 24.45 | 0.27 | 0.11 | 1.1 | 1.07 | 1 | 0.035 |
| GhUBC1__$T_3$-1__7 | 23.27 | 0.46 | 0.19 | 2 | | | |
| GhUBC1__$T_3$-31__10 | 21.42 | 0.46 | 0.16 | 2.1 | | | |
| GhUBC1__Bt-cotton | 24.15 | 0.79 | 0.35 | 3.3 | | | |

SD—standard deviation;
SE—standard error [SD/SQRT(n)];
CV—coefficient of variation [SD/mean value];
*qRT-PCR reaction for each sample was repeated 6-times and averages values were shown in this table;
**$X_0/R_0 = 10^{[(Ct, X-IX)/SX)]-[(Ct, R-IR)/SR]}$, where X is nptII, R is UBC1, I is intercept of the standard curve, S is slope of the standard curve for target (X) and reference (R) genes (Weng et al., supra);
***Coefficient of variation in copy number estimates was calculated from coefficient of variation estimates for UBC1(endogenous control) and nptII (target gene) using s = (cv)(mean value$_{nptII}$/mean value$_{UBC1}$), where cv = SQRT[(CV$_{nptII}$)$^2$ + (CV$_{UBC1}$)$^2$].

curve for target (X) and reference (R) genes (Weng et al., supra). $X_0/R_0$ values were used directly (i.e. without doubling) for copy number estimation since our samples were $T_3$ generation plants, not $T_0$ as was the case in Weng et al. (supra). Coefficient of variation in copy number estimates were calculated from coefficient of variation estimates for GhUBC1 (endogenous control) and nptII (target gene).

Vector-specific PCR-amplification of selected RNAi plants of $T_3$ generation showed that selected RNAi plants have genomic insertions for pHellsgate-8::PHYA1 RNAi plasmid (FIG. 7B). Further, in quantitative real-time PCR experiment, the correlations coefficients, slopes and PCR-efficiency were highly acceptable (Ginzinger, 2008) for copy number identification. Coefficient of variation for cycle threshold ($C_t$) values ranged only 1.1-4.6% over six repeated amplifications in each dilution series (Table 3). Results showed that PCR-positive RNAi plant from $T_3$-1_7 family have three copies while RNAi plant from $T_3$-31_10 family Example 7

RNA Isolation and Quantitative Real-Time PCR

The total RNAs were isolated from leaf tissues of $T_3$-generation RNAi cotton plants and non RNAi control plants using combination of protocols described by Suzuki et al. (2001. *J. Exp. Bot.* 52:1575-1579) and Wu et al. (2002. *Plant Mol. Biol. Rep.* 20:213-218) with minor modifications. To identify RNAi influence in the expression of PHYA1 genes as well as other cotton phytochrome genes (PHYA2s, PHYBs, PHYCs, and PHYEs), we utilized quantitative real-time PCR (qRT-PCR) method using SYBR-green based amplicon detection. We synthesized cDNAs from the non-RNAi Coker 312 and the same RNAi plants that were used for copy number identification and phenotypic evaluations. Control and RNAi plants were grown in the same greenhouse environment and under same light conditions. For creation of standard curves for each gene used in qRT-PCR analysis, 2-fold dilution series (1, 2 up to 128×) of 1:15 diluted cDNA from control Coker 312 was created. Average $C_t$ values from at least, 2 were plotted against log of starting amount to obtain standard curves. Efficiencies of amplification were calculated based on slopes of standard curves with the formula: $E=10^{(-1/slope)}-1$ (Ginzinger, 2008). Slope and Intercept indices from the standard curves obtained for each gene analyzed were used to calculate log input amount [Log input amount=(Average $Ct_{target\ gene}$–Intercept$_{target\ gene}$)/Slope$_{target\ gene}$]; then, the input amount was calculated using $10^{log\ input\ amount}$. Input amounts obtained for phytochrome genes were divided by input amount for endogenous control gene GhPP2A1 (Artico et al. 2010. BMC Plant Bio. 21:10-49). Relative quantity of the target genes then was calculated by dividing normalized quantity of target gene expression in RNAi plants by the normalized quantity of the same gene expression in control plant, used as a calibrator. Coefficient of variation was calculated from coefficient of variation estimates for GhPP2A1 and each of the phytochromes.

Briefly, 100 mg leaf tissues immediately were frozen in liquid nitrogen and powdered using a pestle and mortar, followed by adding of 2 mL hot extraction buffer of Wu et al. (supra), heated to 80° C. and with 10 mM DTT freshly added. Then, 60 µL of 25 mg/mL proteinase K was added to the homogenate and ground further to mix. A homogenate was mixed very well, transferred 2 mL plastic tubes, kept at the room temperature for 15 min and centrifuged (Eppendorf 5415R, Germany) at top speed for 20 min, +4° C. Supernatant was transferred to the fresh 2 mL tubes and followed with conventional water-saturated phenol:chloroform-isoamylacohol RNA precipitation procedure (Chomczynski and Sacchi. 1987. Analyt. Bioch. 162:156-159; Suzuki et al., supra). From this point, all steps were exactly as described and optimized by Suzuki et al. (supra). The resulting RNA pellet was washed by 75% (v/v) ethanol, air dried and dissolved in sterile DEPC-treated water.

To check integrity of RNA, 5 µl total RNA solution were loaded on a 1% agarose gel containing 2.2 M of formaldehyde in the presence of ethidium bromide (Maniatis et al., 1982). The integrity of RNA was judged by the presence and intensity of rRNA bands. Further, total RNA samples were treated with RNAase free rDNAase I (Ambion, USA) according manufacturer's protocol and re-purified with additional purification steps using acid phenol:chloroform (5:1; Ambion, USA) and ethanol precipitation. The concentration of total RNA samples were quantified using spectrophotometer (GENESYS 10UV, Thermo Scientific, USA). The first strand cDNAs were synthesized from ~2 µg total RNAs using Avian RT cDNA kit (Sigma, USA) with random nonamer primers according manufactures protocol. The first strand cDNA synthesized were diluted 1:15 with sterile water and used in RT and qRT-PCR analyses. First, RT-PCR reactions were carried out with intron specific primer pairs (A1341F/R; Table 1; Cronn et al. 2002. Am. J. Bot. 89:707-725) for checking DNA contamination and with primers for catalytic subunit of protein phosphatase 2A gene of cotton (GhPP2A1; Artico et al., 2010) to check the quality of the cDNAs synthesized. RT-PCR reactions were carried out using RT-PCR kit (Sigma, USA) according manufacture's protocol. Samples were subjected to qPCR only if they fail to amplify intronic primer pairs, but not the endogenous reference gene (data not shown). This is to make sure for complete removal of genomic DNAs after rDNAase treatment.

Real-time quantitative PCR was carried out on an Applied Biosystems 7500 real-time PCR systems (Applied Biosystems, Foster city, USA). PCR reactions were performed in 25 µl volume with the following cycling conditions: 95° C. for 10 min, followed by 40 cycles of 95° C. for 15 s and 65° C. for 45 s. Each 25 µl reaction mixture contained 12.5 µl SYBR GREEN Master Mix (2×), 0.35 µl (140 nM) of each primer (10 µM), 6 µl of template 1:15 times diluted cDNA template, and 5.8 µl sterile deionized water. 2×SYBR GREEN PCR master mix contained No AmpErase UNG, AmpliTaq Gold DNA polymerase, deoxynucleoside triphosphates with dUTP and SYBR Green reaction buffer with magnesium chloride (Applied Biosystems, Foster city, USA). Post real-time PCR dissociation curves were constructed for each primer pairs used to evaluate the primer-dimers, genomic DNA contaminations and misannealing issues. Problematic reaction wells were omitted from the analysis. Analysis of qRT-PCR amplifications was conducted using 7500 System SDS v1.4 Software (Applied Biosystems, Foster city, USA).

To quantify relative gene expression in the two RNAi plant families (as shown in FIG. 7), first, we created standard curves for each genes from 2-fold serial dilutions of 1:15 diluted cDNA of the calibrator sample (Coker 312). Results showed that the correlations coefficients and slopes for each targeted genes, as well as PCR-efficiencies (above 95%), for primer pairs of each gene tested were in acceptable ranges (Ginzenger, 2008) to perform a relative quantification (Table 5). Coefficient of variation for cycle threshold ($C_t$) values ranged only 0.2-2.6% and standard deviation values ranged only 0.2-0.7 over repeated amplifications among six gene primer pairs tested, indicating that qRT-PCR system functioned stably and reliably (Table 6).

TABLE 5

Standard curve (STC) for phytochrome gene-specific primers; qRT-PCR.

| Primer pairs | *Slope of STC | Intercept of STC | $R^2$ | **Efficiency, % |
|---|---|---|---|---|
| PHYA1 | −3.05 | 28.66 | 0.99 | 113 |
| PHYA2 | −3.09 | 28.21 | 0.99 | 111 |
| PHYB | −3.21 | 29.28 | 0.99 | 104 |
| PHYC | −3.44 | 31.34 | 0.99 | 95 |
| PHYE | −3.02 | 31.58 | 0.99 | 114 |
| GhPP2A1(endo) | −3.29 | 30.2 | 0.99 | 101 |

*qRT-PCR reaction for each primer was repeated twice and averages values were used for a standard curve creation;
**Efficiency of PCR was calculated using following formula: $E = 10^{(-1/Slope)} - 1$ and presented in percentage.

TABLE 6

Quantitative PCR amplification details for phytochrome genes and endogenous control gene (GhPP2A) in $T_3$ generation RNAi and normal cotton genotypes

| Gene_Sample | Average Ct | SD | SE | CV, % | QPCR repeats |
|---|---|---|---|---|---|
| Cotton phytochrome A1 gene | | | | | |
| $T_3$-1_7 | 26.77 | 0.71 | 0.35 | 2.6 | 4 |
| $T_3$-31_10 | 23.17 | 0.05 | 0.025 | 0.2 | 4 |
| Coker-312 | 23.23 | 0.14 | 0.07 | 0.6 | 4 |
| Cotton phytochrome A2 gene | | | | | |
| $T_3$-1_7 | 24.1 | 0.19 | 0.093 | 0.8 | 4 |
| $T_3$-31_10 | 22.12 | 0.097 | 0.043 | 0.4 | 5 |
| Coker-312 | 22.89 | 0.12 | 0.055 | 0.5 | 5 |

TABLE 6-continued

Quantitative PCR amplification details for phytochrome genes and endogenous control gene (GhPP2A) in $T_3$ generation RNAi and normal cotton genotypes

| Gene_Sample | Average Ct | SD | SE | CV, % | QPCR repeats |
|---|---|---|---|---|---|
| Cotton phytochrome B gene | | | | | |
| $T_3$-1_7 | 23.74 | 0.08 | 0.04 | 0.3 | 4 |
| $T_3$-31_10 | 23.55 | 0.113 | 0.05 | 0.5 | 5 |
| Coker-312 | 23.87 | 0.15 | 0.06 | 0.6 | 6 |
| Cotton phytochrome C gene | | | | | |
| $T_3$-1_7 | 24.33 | 0.23 | 0.11 | 0.9 | 4 |
| $T_3$-31_10 | 24.18 | 0.09 | 0.40 | 0.4 | 5 |
| Coker-312 | 25.37 | 0.40 | 0.16 | 0.2 | 6 |
| Cotton phytochrome E gene | | | | | |
| $T_3$-1_7 | 24.6 | 0.6 | 0.27 | 2.4 | 5 |
| $T_3$-31_10 | 24.2 | 0.29 | 0.14 | 1.2 | 4 |
| Coker-312 | 26.62 | 0.54 | 0.22 | 2.0 | 6 |
| Catalytic subunit of protein phosphatase 2A of cotton (GhPP2A1, endogenous control) | | | | | |
| $T_3$-1_7 | 26.65 | 0.44 | 0.25 | 1.6 | 3 |
| $T_3$-31_10 | 24.07 | 0.20 | 0.09 | 0.8 | 5 |
| Coker-312 | 24.54 | 0.34 | 0.14 | 1.4 | 6 |

SD—standard deviation;
SE—standard error [SD/SQRT(n)];
CV—coefficient of variation [SD/mean value]

Transformation and integration of the pHellsgate-8::PHYA1 RNAi vector affected the expression of several cotton phytochrome genes (Table 1; Table 7). PHYA1 gene expression was suppressed by 70% in $T_3$-1_7, and 24% in $T_3$-31_10 family. The PHYA1 RNAi construct did not suppress the expression of other phytochrome genes tested with the exception of a slight (10%) down-regulation of PHYB in $T_3$-31_10. Rather, we detected 2 to 20-fold overexpression of PHYA2, PHYB (in $T_3$-1_7 sample only), PHYC, and PHYE genes in both RNAi plant samples. Intriguingly, high level of overexpression of other phytochromes genes tested was more evident in $T_3$-1_7 sample, where the deeper suppression of PHYA1 gene expression was detected compared to the other RNAi sample $T_3$-31_10 (Table 7).

TABLE 7

Relative quantity estimation for $T_3$ RNAi cotton lines and control sample

| Gene_Sample | Average log input amount (CV, %) | Average input amount | Normalized amount against PP2A | Relative quantity ± CV* |
|---|---|---|---|---|
| Cotton phytochrome A1 gene | | | | |
| $T_3$-1_7 | 0.6 (3.7) | 4.17 | 0.35 | 0.3 ± 0.12 |
| $T_3$-31_10 | 1.8 (0.9) | 63.2 | 0.87 | 0.76 ± 0.03 |
| Coker 312 (calibrator) | 1.8 (2.6) | 60.1 | 1.15 | 1.0 ± 0.07 |
| Cotton phytochrome A2 gene | | | | |
| $T_3$-1_7 | 1.3 (4.5) | 21.37 | 1.78 | 1.77 ± 0.23 |
| $T_3$-31_10 | 2.0 (1.6) | 93.6 | 1.28 | 1.27 ± 0.05 |
| Coker 312 (calibrator) | 1.7 (2.3) | 52.9 | 1.01 | 1.0 ± 0.06 |
| Cotton phytochrome B gene | | | | |
| $T_3$-1_7 | 1.7 (1.5) | 53.12 | 4.43 | 4.81 ± 0.60 |
| $T_3$-31_10 | 1.8 (2.0) | 60.8 | 0.83 | 0.9 ± 0.03 |
| Coker 312 (calibrator) | 1.7 (2.8) | 48.4 | 0.92 | 1.0 ± 0.07 |

TABLE 7-continued

Relative quantity estimation for $T_3$ RNAi cotton lines and control sample

| Gene_Sample | Average log input amount (CV, %) | Average input amount | Normalized amount against PP2A | Relative quantity ± CV* |
|---|---|---|---|---|
| Cotton phytochrome C gene | | | | |
| $T_3$-1_7 | 2.0 (3.3) | 108.87 | 9.09 | 8.75 ± 1.12 |
| $T_3$-31_10 | 2.1 (1.3) | 120.5 | 1.65 | 1.59 ± 0.06 |
| Coker 312 (calibrator) | 1.7 (6.7) | 54.5 | 1.04 | 1.0 ± 0.09 |
| Cotton phytochrome E gene | | | | |
| $T_3$-1_7 | 2.3 (8.6) | 204.3 | 17.05 | 20.4 ± 3.07 |
| $T_3$-31_10 | 2.4 (3.9) | 277.2 | 3.8 | 4.54 ± 0.23 |
| Coker 312 (calibrator) | 1.6 (10.9) | 43.8 | 0.84 | 1.0 ± 0.12 |
| Catalytic subunit of protein phosphatase 2A of cotton GhPP2A1 (endogenous control) | | | | |
| $T_3$-1_7 | 1.1 (1.2) | 12 | | |
| $T_3$-31_10 | 1.9 (3.3) | 73 | | |
| Coker 312 (calibrator) | 1.7 (6.1) | 52.5 | | |

*Coefficient of variation for relative quantities was calculated from coefficient of variation estimates of the average log input amount for endogenous control and each target gene using $s = (cv)(mean\ value_{target}/mean\ value_{endo})$, where $cv = SQRT[(CV_{\_TARGET})^2 + (CV_{\_ENDO})^2]$.

Example 8

Figure 9:
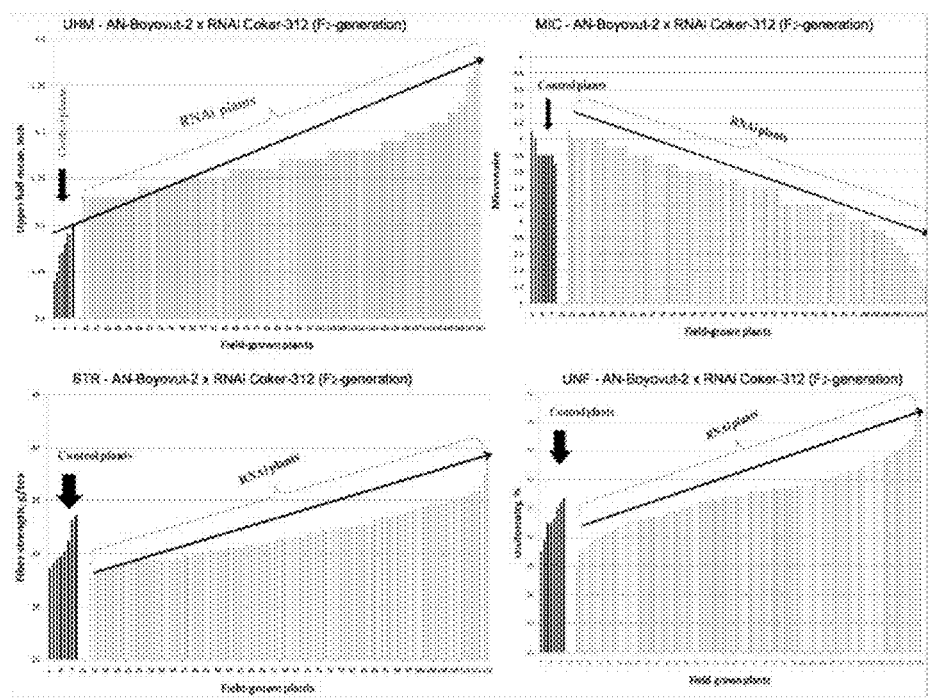
FIG. 9 shows a general trend of changing the major fiber quality traits in second generation AN-Boyovut-2×RNAi Coker-312 hybrids, compared to controls grown under the same conditions.

Genetic Transfer of Phytochrome-Specific RNAi Effects Via Conventional Genetic Crosses When we crossed $T_0$-generation RNAi Coker 312 plants with four commercial varieties of Uzbekistan cotton (Namangan-77, AN-Boyovut-2, C-6524 and Tashkent-6) and evaluated $F_1$ and $F_2$ generation hybrids from these crosses we found notably changed plant architecture with elongated petioles and fruiting branches, greater mean number of flowers and bolls and the plants flowered and matured an average of 5-10 days early compared to control plants (original variety) grown side-by-side in the same field conditions. We also observed more anthocyanin pigmentation in RNAi hybrids (FIG. 8). Measurement of the fiber characteristics using HVI system confirmed that in the $F_2$-generation hybrids of all above-mentioned varieties, fiber quality was markedly improved. For instance, in $F_2$-generation hybrids of one of the widely grown variety of Uzbekistan, AN-Boyovut-2, fiber quality traits (FIG. 9) were improved similarly to what was observed with $T_2$ and $T_3$ generations of RNAi Coker-312 plants. In $F_2$-generation hybrids of AN-Boyovut-2×RNAi Coker 312, we observed high quality RNAi genotypes with UHM of 1.37 inch, MIC of 3.8, STR of 31.5 g/tex, and UI 90%. The same-field grown control AN-Boyovut-2 plants had an average UHM of 1.17 inch, MIC of 4.9, STR of 30 g/tex and UI of 86%. A similar trend of fiber trait improvement as well as flowering and root development improvement were observed in $F_2$ and $F_3$ generations of other variety crosses (data not shown). Although the lint percentage, lint and seed indexes were smaller in hybrids, we observed 6-13 kg/0.010 ha more seed cotton yield in $F_3$ RNAi hybrid families of different variety crosses compared to the same field grown original parental versions, suggesting a potential of 18-40% seed cotton yield increase. Thus, the constructs were integrated into the genome and transmitted through the sexual cycle and plants could be selected that exhibited very similar trait measurements to the original T₃ RNAi transformed plants.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A nucleic acid construct comprising a portion of the PHYA1 gene of *Gossypium hirsutum*, wherein said portion is the DNA sequence of SEQ ID NO: 1 consisting of 213 consecutive sense nucleotide base pairs and the antisense-complement thereof that are transcribed into a ribonucleic acid to form a hairpin-like double stranded ribonucleic RNAi molecule.

2. A recombinant binary vector comprising a PHYA1 construct encoding a RNAi molecule wherein said construct comprises a portion of the PHYA1 gene of *Gossypium hirsutum*, wherein said portion is the DNA sequence of SEQ ID NO: 1 consisting of 213 consecutive sense nucleotide base pairs and the antisense-complement thereof that are transcribed into a ribonucleic acid to form a hairpin-like double stranded ribonucleic RNAi molecule, wherein said vector comprises the 35S promoter of Cauliflower mosaic virus (CAMV) immediately upstream of the portion of the PHYA1 gene, and wherein said construct is delivered by *Agrobacterium*-mediated inoculation, resulting in recombination in vitro, and the suppression of PHYA1 genes and altered expression levels of other cotton phytochrome genes.

3. A host cell comprising the recombinant binary vector comprising the PHYA1 construct encoding the RNAi molecule of claim 2.

4. The host cell of claim 3, wherein said host cell is a cotton plant cell.

5. The host cell of claim 4, wherein said host cell is a cell from any one of *G. hirsutum, G. barbadense, G. herbaceum* and *G. raimondii*.

6. A transgenic cotton plant cell comprising the PHYA1 RNAi construct of claim 2.

7. A transgenic cotton plant comprising the PHYA1 RNAi construct of claim 2, wherein the transgenic plant exhibits cotton fibers of increased length and strength as well as improved micronaire, elongation and fiber uniformity relative to the wild-type cotton plant.

8. Plants, plant cells, and plant parts, and plant seeds from any one of *Gossypium hirsutum, G. barbadense, G. herbaceum* and *G. raimondii* which have been transformed with and comprise the PHYA1 RNAi construct of claim 2.

9. A method to down-regulate expression of the phytochrome PHYA1 gene using RNA interference to generate novel transgenic plants, comprising:
   a) planting surface sterilized cottonseeds into agar medium,
   b) keeping the seeds under dark conditions for germination,
   c) placing germinated seeds under a photoperiodic condition of 16 hr light followed by 8 hr dark for the development of seedlings, d) isolating hypocotyl sections from said seedlings,
e) wounding said hypocotyl sections in several places,
f) applying a suspension comprising the recombinant binary vector of claim 2 onto wounded hypocotyl sections, and incubating in the dark,
g) transferring infected hypocotyl sections to selective medium containing kanamycin and culturing under a 16 h photoperiod,
h) transferring the 3 mm callus transgenic tissues resistant to the selective marker kanamycin to new medium and growing them to the somatic embryo stage,
i) culturing them to obtain transgenic embryonic plantlets with roots and leaves,
j) selecting plants exhibiting improved cotton fiber quality, early-flowering and early boll maturity, enhanced root elongation, and increased seed cotton production,
k) growing and breeding said plants exhibiting advantageous characteristics to the T3 generation,
l) determining the copy number of the integrated transgene vector sequence, and
m) establishing that the number of copies of PHYA1 RNAi constructs of the invention can alter the level of the suppression of PHYA1 and also the level of expression of the PHYB/C/E phytochrome genes, thereby leading to an alteration in plant characteristics in said cotton plants.

10. The method of claim 9 where said transgenic plants are from any one of *Gossypium hirsutum, G. barbadense, G. herbaceum* and *G. raimondii*.

11. A transgenic cotton plant cell of any one of *Gossypium hirsutum, G. barbadense, G. herbaceum* and *G. raimondii* comprising the PHYA1 RNAi construct of claim 2, wherein the transgenic plant regenerated from said cell exhibits suppression of the PHYA1 gene and overexpression of the PHYB/C/E genes resulting in a plant demonstrating changed plant architecture, said plant exhibiting one or more of the following characteristics: elongated leaf petioles, elongated fruit branches, elongated boll peduncles and elongated root system, vigorous vegetative growth, early flowering and early boll maturity, senescence-enhanced anthocyanin pigmentation in stems and leaves, increased seed cotton yield, and one or more of the characteristics of improved fiber quality, wherein said characteristics are strength, micronaire, elongation and uniformity, compared to wild-type non-transformed cotton plant.

12. A method for reducing the level of phytochrome A1 in a cotton plant, the method comprising expressing in the plant a heterologous nucleic acid construct comprising a portion of the PHYA1 gene of *Gossypium hirsutum*, wherein said portion is the DNA sequence of SEQ ID NO: 1 consisting of 213 consecutive sense nucleotide base pairs and the anti-sense-complement thereof that are transcribed into a ribonucleic acid to form a hairpin-like double stranded ribonucleic RNAi molecule, wherein expression induces RNA interference in the plant resulting in a plant which produces long fibers exhibiting one or more of the characteristics of improved fiber quality, wherein said characteristics are strength, micronaire, elongation and uniformity.

13. A transgenic cotton plant produced by the method of claim 12 or the progeny thereof, wherein said plant or progeny thereof comprises the heterologous nucleic acid construct and exhibits altered expression of photomorphogenic characteristics including changed plant architecture, said plant exhibiting one or more of the following characteristics: elongated leaf petioles, elongated fruit branches, elongated boll peduncles and elongated root system, vigorous vegetative growth, early flowering and early boll maturity, senescence-enhanced anthocyanin pigmentation in stems and leaves, increased seed cotton yield, and one or more of the characteristics of improved fiber quality, wherein said characteristics are strength, micronaire, elongation and uniformity, compared to wild-type non-transformed cotton plant.

14. A transgenic seed of the transgenic plant of claim 13, comprising the PHYA1 RNAi construct of the invention.

15. A method of using the transgenic plant of any one of claims 13, 7, 8 and 10 in conventional breeding to produce more transgenic cotton plants comprising the recombinant binary vector or heterologous nucleic acid construct.

16. A plant resulting from said conventional breeding of the method of claim 15 wherein said transgenic plant is crossed with another transgenic cotton plant and comprises the recombinant binary vector or heterologous nucleic acid construct.

17. A plant resulting from said conventional breeding of the method of claim 15 wherein said transgenic plant is crossed with any one of the commercial varieties of Uzbekistan cotton: Namangan-77, AN-Boyovut-2, C-6524 and Tashkent-6 and comprises the recombinant binary vector or heterologous nucleic acid to reduce expression of PHYA1.

18. A method for reducing the level of phytochrome A1 in a cotton plant, the method comprising expressing in the plant a heterologous nucleic acid construct comprising a portion of the PHYA1 gene of *Gossypium hirsutum*, wherein said portion is the DNA sequence of SEQ ID NO: 1 consisting of 213 consecutive sense nucleotide base pairs and the anti-sense-complement thereof that are transcribed into a ribonucleic acid to form a hairpin-like double stranded ribonucleic RNAi molecule, wherein expression induces RNA interference in the plant resulting in a plant or progeny of said plant exhibiting one or more of the characteristics: elongated leaf petioles, elongated fruit branches, elongated boll peduncles and elongated root system, vigorous vegetative growth, early flowering and early boll maturity, senescence-enhanced anthocyanin pigmentation in stems and leaves, increased seed cotton yield, and one or more of the characteristics of improved fiber quality, wherein said characteristics are strength, micronaire, elongation and uniformity, relative to a wild-type cotton plant cultivated in normal solar light.

19. A method for stimulating expression levels of the phytochrome genes PHYB, PHYD and PHYE in a cotton plant, the method comprising expressing in the plant a heterologous nucleic acid construct comprising a portion of the PHYA1 gene of *Gossypium hirsutum*, wherein said portion is the DNA sequence of SEQ ID NO: 1 consisting of 213 consecutive sense nucleotide base pairs and the anti-sense-complement thereof that are transcribed into a ribonucleic acid to form a hairpin-like double stranded ribonucleic RNAi molecule, wherein the expression induces RNA interference in the plant resulting in altered expression levels of PHYB, PHYD and PHYE.

\* \* \* \* \*

SEQUENCE LISTING

```
<160> NUMBER OF SEQ ID NOS: 28

<210> SEQ ID NO 1
<211> LENGTH: 213
<212> TYPE: DNA
<213> ORGANISM: Gossypium hirsutum

<400> SEQUENCE: 1
gtccgtatga tcgttgattg tcgagcaaaa catgtgcaag tatttcaaga tgataagctt      60
cctatggacc taacyttgtg tggttcaacc ctgagggctc cccatagctg ccatttacag     120
tacatggara acatgaattc cattgcttct ctggttatgg ctgtcatcgt caatgatgga     180
gatgaagaag gtgatgggac taactccgag cag                                  213

<210> SEQ ID NO 2
<211> LENGTH: 71
<212> TYPE: PRT
<213> ORGANISM: Gossypium hirsutum

<400> SEQUENCE: 2

Val Arg Met Ile Val Asp Cys Arg Ala Lys His Val Gln Val Phe Gln
1               5                   10                  15

Asp Asp Lys Leu Pro Met Asp Leu Thr Leu Cys Gly Ser Thr Leu Arg
            20                  25                  30

Ala Pro His Ser Cys His Leu Gln Tyr Met Glu Asn Met Asn Ser Ile
        35                  40                  45

Ala Ser Leu Val Met Ala Val Ile Val Asn Asp Gly Asp Glu Glu Gly
    50                  55                  60

Asp Gly Thr Asn Ser Glu Gln
65                  70

<210> SEQ ID NO 3
<211> LENGTH: 52
<212> TYPE: DNA
<213> ORGANISM: Artificial Sequence
<220> FEATURE:
<223> OTHER INFORMATION: Chemically Synthesized

<400> SEQUENCE: 3
ggggacaagt ttgtacaaaa aagcaggctg tgctcggagt tagtcccatc ac              52

<210> SEQ ID NO 4
<211> LENGTH: 51
<212> TYPE: DNA
<213> ORGANISM: Artificial Sequence
<220> FEATURE:
<223> OTHER INFORMATION: Chemically Synthesized

<400> SEQUENCE: 4
gggaccactt tgtacaagaa agctgggtgt ccgtatgatt gttgattgtc g               51

<210> SEQ ID NO 5
<211> LENGTH: 20
```

```
<212> TYPE: DNA
<213> ORGANISM: Artificial Sequence
<220> FEATURE:
<223> OTHER INFORMATION: Chemically Synthesized

<400> SEQUENCE: 5
gttcatttca tttggagagg                                             20

<210> SEQ ID NO 6
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 6
cgtcttacac atcacttgtc                                             20

<210> SEQ ID NO 7
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 7
cttacatttg gattgattac ag                                          22

<210> SEQ ID NO 8
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 8
cgcatatctc attaaagcag                                             20

<210> SEQ ID NO 9
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 9
gatagcggtc cgccacac                                               18

<210> SEQ ID NO 10
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 10
tttccaccat gatattcggc aagcagg                                     27

<210> SEQ ID NO 11
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 11
```

```
cgaggatctc gtcgtgacac at                                              22

<210> SEQ ID NO 12
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 12
tggcattata ttgtcattgt tactatcc                                        28

<210> SEQ ID NO 13
<211> LENGTH: 28
<212> TYPE: DNA
<213> ORGANISM: Artificial Sequence
<220> FEATURE:
<223> OTHER INFORMATION: Chemically Synthesized

<400> SEQUENCE: 13
cttaaatttc caagcagcag cagaagcc                                        28

<210> SEQ ID NO 14
<211> LENGTH: 29
<212> TYPE: DNA
<213> ORGANISM: Artificial Sequence
<220> FEATURE:
<223> OTHER INFORMATION: Chemically Synthesized

<400> SEQUENCE: 14
accatgttat cttattctaa gacaagctc                                       29

<210> SEQ ID NO 15
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 15
gttgtccttg gcattgcag                                                  19

<210> SEQ ID NO 16
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 16
ttttcatgga gatcccggtt c                                               21

<210> SEQ ID NO 17
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 17
gttcaccttg cacatttgga g                                               21

<210> SEQ ID NO 18
<211> LENGTH: 20
<212> TYPE: DNA
<213> ORGANISM: Artificial Sequence
```

<220> FEATURE:
<223> OTHER INFORMATION: Chemically Synthesized

<400> SEQUENCE: 18
cctgcttccc tcaagtactg                          20

<210> SEQ ID NO 19
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 19
tgcagaatta acaggactct cag                      23

<210> SEQ ID NO 20
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 20
ttactagagc aagcgttcac c                        21

<210> SEQ ID NO 21
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 21
agctcaacca ttaagtctct gtg                      23

<210> SEQ ID NO 22
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 22
ttgctcactg tccatctcat c                        21

<210> SEQ ID NO 23
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 23
gccatgcaaa tccggttaag                          20

<210> SEQ ID NO 24
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 24
aacgactgcc atcactaacg                          20

```
<210> SEQ ID NO 25
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 25
gatccttgtg gaggagtgga                                               20

<210> SEQ ID NO 26
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 26
gcgaaacagt tcgacgagat                                               20

<210> SEQ ID NO 27
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 27
gcatgctgaa ttgacagaac cagcy                                         25

<210> SEQ ID NO 28
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 28
cactcacaaa gttatgccgg atgy                                          24
```